(12) United States Patent
Aoki et al.

(10) Patent No.: US 10,441,154 B2
(45) Date of Patent: Oct. 15, 2019

(54) CAMERA SYSTEM FOR MONITORING INSIDE OF BODY AND AUXILIARY DEVICE AND METHOD FOR INSTALLING IMAGING APPARATUS FOR MONITORING INSIDE OF BODY

(71) Applicant: Sharp Kabushiki Kaisha, Sakai-shi, Osaka (JP)

(72) Inventors: Hitoshi Aoki, Sakai (JP); Kishoh Takamatsu, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 215 days.

(21) Appl. No.: 15/111,514

(22) PCT Filed: Dec. 25, 2014

(86) PCT No.: PCT/JP2014/084251
§ 371 (c)(1),
(2) Date: Jul. 14, 2016

(87) PCT Pub. No.: WO2015/107848
PCT Pub. Date: Jul. 23, 2015

(65) Prior Publication Data
US 2016/0331222 A1    Nov. 17, 2016

(30) Foreign Application Priority Data
Jan. 16, 2014    (JP) ................. 2014-006147

(51) Int. Cl.
*A61B 1/313*    (2006.01)
*A61B 1/00*    (2006.01)
(Continued)

(52) U.S. Cl.
CPC ........ *A61B 1/3132* (2013.01); *A61B 1/00018* (2013.01); *A61B 1/00147* (2013.01);
(Continued)

(58) Field of Classification Search
CPC ...... A61B 2017/00283; A61B 1/00147; A61B 1/313; A61B 1/3132; A61B 5/6861;
(Continued)

(56) References Cited

U.S. PATENT DOCUMENTS

2008/0309758 A1    12/2008    Karasawa et al.
2008/0312500 A1    12/2008    Asada et al.
(Continued)

FOREIGN PATENT DOCUMENTS

JP    2008-307226 A    12/2008
JP    2009-172053 A    8/2009
(Continued)

OTHER PUBLICATIONS

Aoki et al., "Camera System for Monitoring Inside of Body", U.S. Appl. No. 15/546,291, filed Jul. 26, 2017.
(Continued)

*Primary Examiner* — Ryan N Henderson
(74) *Attorney, Agent, or Firm* — Keating & Bennett, LLP

(57) ABSTRACT

A camera system for monitoring the inside of a body, which is easily used and can be installed during a short period of time, is suggested. A drawing auxiliary tool (7) having a wire structure guides a camera unit (11) and a camera side cable (12) in which one end part is connected to the camera unit (11) from the outside of the body toward the inside of the body via a first hole provided on a body wall, and draws out the other end part of the camera side cable (12) from the inside of the body toward the outside of the body via a second hole provided on the body wall.

6 Claims, 20 Drawing Sheets

(51) Int. Cl.
*A61B 1/04* (2006.01)
*A61B 90/00* (2016.01)
*A61B 17/00* (2006.01)

(52) U.S. Cl.
CPC .......... *A61B 1/00154* (2013.01); *A61B 1/041* (2013.01); *A61B 90/361* (2016.02); *A61B 1/00124* (2013.01); *A61B 1/313* (2013.01); *A61B 2017/00283* (2013.01)

(58) Field of Classification Search
CPC . A61B 2562/162; A61B 1/267; A61B 1/2673; A61B 1/2676; A61B 1/041; A61B 1/042; A61B 1/043; A61B 1/045
See application file for complete search history.

(56) References Cited

U.S. PATENT DOCUMENTS

| | | | |
|---|---|---|---|
| 2009/0076325 A1* | 3/2009 | Yokoi | A61B 1/00147 600/118 |
| 2009/0187073 A1 | 7/2009 | Karasawa et al. | |
| 2011/0046440 A1 | 2/2011 | Asada et al. | |
| 2016/0143510 A1 | 5/2016 | Gotoh et al. | |
| 2016/0331222 A1 | 11/2016 | Aoki et al. | |

FOREIGN PATENT DOCUMENTS

| | | | | |
|---|---|---|---|---|
| JP | 4472727 B2 | 6/2010 | | |
| JP | 4599474 B1 | 12/2010 | | |
| JP | 2011-156267 A | 8/2011 | | |
| JP | 2011156267 A * | 8/2011 | | A61B 1/041 |
| JP | 2012-239519 A | 12/2012 | | |
| JP | 2012239519 A * | 12/2012 | | A61B 1/041 |
| JP | 6019253 B2 | 11/2016 | | |
| WO | 2015/020124 A1 | 2/2015 | | |
| WO | 2015/064743 A1 | 5/2015 | | |
| WO | 2015/080148 A1 | 6/2015 | | |
| WO | 2015/080293 A1 | 6/2015 | | |

OTHER PUBLICATIONS

Gotoh et al., "In-Body Monitoring Camera System and Support Tube for In-Body Monitoring-Camera-System", U.S. Appl. No. 14/899,269, filed Dec. 17, 2015.

Inoue et al., "In-Vivo Monitoring Camera System, and Support Tube for In-Vivo Monitoring Camera System", U.S. Appl. No. 15/031,777, filed Apr. 25, 2016.

Urakawa et al., "Intracorporeal-Monitoring Camera System, Support Tube for Intracorporeal-Monitoring Camera System, and Cable Holder for Intracorporeal-Monitoring Camera System", U.S. Appl. No. 14/917,064, filed Mar. 7, 2016.

Urakawa et al., "Camera System for Monitoring Inside of Body, Accessory for Support Tube of Camera System for Monitoring Inside of Body, Fixing Tool for Camera System for Monitoring Inside of Body, and Method for Installing Camera System for Monitoring Inside of Body", U.S. Appl. No. 15/031,816, filed Apr. 25, 2016.

Aoki et al., "In-Body Monitoring Camera System and Camera Unit", U.S. Appl. No. 15/129,044, filed Sep. 26, 2016.

Aoki et al., "Camera System for Monitoring Inside of Body and Auxiliary Tool Set", U.S. Appl. No. 15/112;726, filed Jul. 20, 2016.

Official Communication issued in International Patent Application No. PCT/JP2014/084251, dated Apr. 7, 2015.

* cited by examiner

1 CAMERA SYSTEM FOR MONITORING INSIDE OF BODY
2 IMAGING APPARATUS
3 CONTROL SYSTEM
4 CONNECTION UNIT
5 DRAWING AUXILIARY TOOL
6 PUNCTURING DEVICE
7 WIRE-LIKE DRAWING AUXILIARY TOOL
8 DRAWING AUXILIARY TOOL CONNECTION UNIT
9 WIRE
10 PULLING UNIT
11 CAMERA UNIT
12 CAMERA SIDE CABLE
15 CABLE CONNECTOR
16 EQUIPMENT SIDE CABLE
17 CAMERA UNIT CONTROL EQUIPMENT
18 DISPLAY
41 BODY WALL

FIG. 16

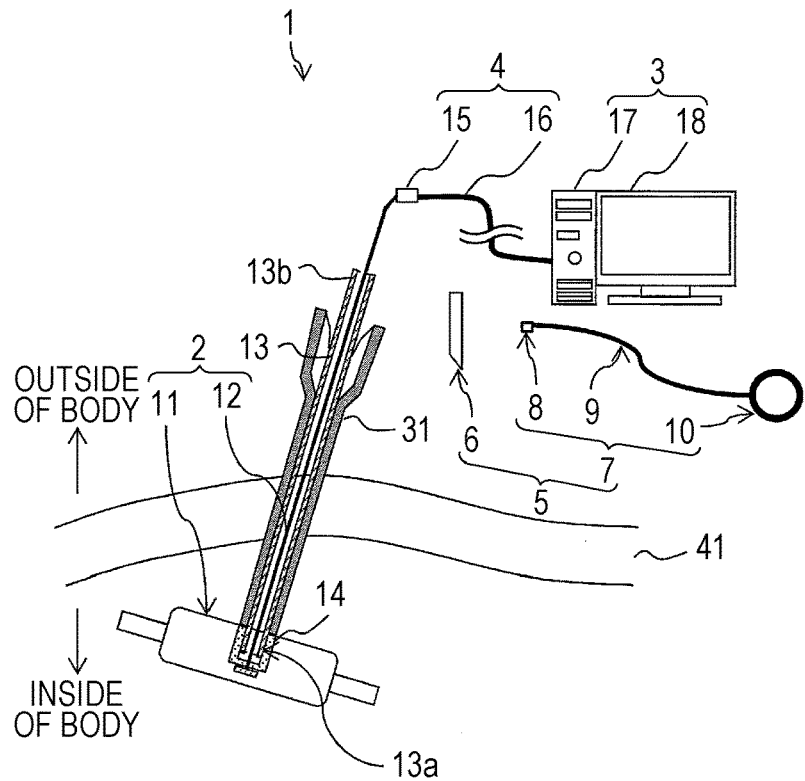

1 CAMERA SYSTEM FOR MONITORING INSIDE OF BODY
2 IMAGING APPARATUS
3 CONTROL SYSTEM
4 CONNECTION UNIT
5 DRAWING AUXILIARY TOOL
6 PUNCTURING DEVICE
7 WIRE-LIKE DRAWING AUXILIARY TOOL
8 DRAWING AUXILIARY TOOL CONNECTION UNIT
9 WIRE
10 PULLING UNIT
11 CAMERA UNIT
12 CAMERA SIDE CABLE
13 CAMERA SUPPORT TUBE
13a END PART
13b END PART
14 SUPPORT TUBE JOINING UNIT
15 CABLE CONNECTOR
16 EQUIPMENT SIDE CABLE
17 CAMERA UNIT CONTROL EQUIPMENT
18 DISPLAY
41 BODY WALL

CAMERA SYSTEM FOR MONITORING INSIDE OF BODY AND AUXILIARY DEVICE AND METHOD FOR INSTALLING IMAGING APPARATUS FOR MONITORING INSIDE OF BODY

TECHNICAL FIELD

The present invention relates to a camera system for monitoring the inside of a body provided with an imaging part which can be guided toward the inside of a body, and an auxiliary device.

BACKGROUND ART

Endoscopic surgery is minimally invasive surgery for performing examination or medical treatment without laparotomy with respect to a patient. In the endoscopic surgery, a treatment tool, such as forceps, and an endoscope are separately guided toward the inside of a body cavity of the patient, and a practitioner captures an image of a tip end part of the treatment tool inserted into the body cavity within an observation visual field of the endoscope, and performs the treatment operation while observing a treatment state of the patient by the treatment tool using the endoscope. In the endoscopic surgery, the treatment tool and the endoscope are guided toward the inside of the body cavity through a pipe (a tube-like member which is referred to as a so-called trocar) punctured through a body wall (for example, an abdominal wall) in an abdomen or the like of the patient.

The practitioner substantially narrows the visual field in order to enlarge the image by making the endoscope approach an organ when making an incision or suturing the organ. Therefore, an apparatus which can widely grasp a state outside the work region (for example, the movement of the treatment tool, a bleeding site, and a residual, such as gauze, outside a work region), is required.

Corresponding to such a request, in PTL 1, an apparatus which directly inserts a needle-like connector electrode into an abdominal wall, and joins the connector electrode and a camera to each other in a body, or reversely an apparatus which inserts the needle-like connector electrode into the abdominal wall from the inside of the body, and joins the connector electrode and the camera to each other on the outside of the body, is disclosed.

In PTL 2, an apparatus which inserts a camera unit and a communication cable which joins with the camera unit from a trocar, draws out a needle and the communication cable from an abdominal wall hole toward the outside of a body in a state where an end part of the communication cable is hooked to the needle inserted from the abdominal wall hole, and fixes the communication cable, is disclosed.

CITATION LIST

Patent Literature

PTL 1: Japanese Patent No. 4472727 (issued on Jun. 2, 2010)
PTL 2: Japanese Patent No. 4599474 (issued on Dec. 15, 2010)

SUMMARY OF INVENTION

Technical Problem

However, in PTL 1, since the needle-like connector electrode is directly inserted into the abdominal wall and the connector electrode and the camera join with each other in the body, there is a concern that a foreign substance is mixed into a joining unit of the connector electrode and the camera, and an electric connection failure occurs. In addition, regarding a method for inserting the needle-like connector electrode into the abdominal wall from the inside of the body, by a method for gripping the camera using gripping forceps, easy installation is not possible since it is difficult to apply a sufficient force which pierces through the abdominal wall to the needle-like connector electrode. Therefore, in order to insert the needle-like connector electrode into the abdominal wall, dedicated forceps which support the needle-like connector electrode become necessary, and installation by a simple technique is not possible. In addition, when a position of the dedicated forceps and an installation position of the camera are close to each other, it is difficult to input the force in the installation direction since there is a limit in an operation angle of the dedicated forceps, and the installation becomes difficult. If a work operation is wrong, a serious risk, such as damage of the organ, follows.

In PTL 2, the communication cable is fixed to be drawn out to the outside of the body, but in order to perform an operation of hooking an end part of the communication cable to the needle by an endoscopic camera which does not have depth perception, it is difficult to hook the communication cable to a hook, and it is not easy to draw out the communication cable toward the outside of a body.

Considering the above-described problems, an object of the present invention is to suggest a camera system for monitoring the inside of a body which is easily used and can be installed during a short period of time, an auxiliary device, and a method for installing the camera system for monitoring the inside of a body.

Solution to Problem

In order to solve the above-described problems, there is provided a camera system for monitoring the inside of a body according to an aspect of the present invention, including: an imaging part for monitoring the inside of a body; a control system which is provided on the outside of the body, and includes at least a display apparatus; a cable in which one end part is connected to the imaging part; and an auxiliary device having a wire structure, in which the auxiliary device guides the imaging part and the cable from the outside of the body toward the inside of the body via a first hole provided on a body wall, and draws the other end part of the cable from the inside of the body toward the outside of the body via a second hole provided on the body wall.

In order to solve the above-described problems, there is provided an auxiliary device according to another aspect of the present invention which is used for installing an imaging part on the inside of the body, in a camera system for monitoring the inside of a body including the imaging part for monitoring the inside of a body, a control system which is provided on the outside of the body, and includes at least a display apparatus, and a cable (i) one end part of which is connected to the imaging part, (ii) at the other end part of which a connector is provided, the auxiliary tool including: a wire structure, in which a connection unit is provided at one end part of the auxiliary device and has a shape which is capable of fixing the connector.

In order to solve the above-described problems, there is provided a method for installing an imaging apparatus for monitoring the inside of a body according to still another aspect of the present invention, which is a method for installing an imaging apparatus for monitoring the inside of a body including an imaging part for monitoring the inside of a body, and a cable in which one end part is connected to the imaging part, the method including: a process of providing a first hole on a body wall by using a puncturing device having a cavity on the inside thereof; a process of inserting one end part of a wire-like auxiliary device into the inside of the body via the first hole; a process of drawing out the one end part of the auxiliary device toward the outside of the body via a second hole provided on the body wall; a process of connecting the one end part of the auxiliary device and the cable connected to the imaging part on the outside of the body; and a process of drawing in the imaging part and the cable into the inside of the body via the second hole by pulling the other end part of the auxiliary device, and drawing out the end part of the cable toward the outside of the body via the first hole.

Advantageous Effects of Invention

According to one aspect of the present invention, it is possible to simply perform the entire connecting work of the cable while directly checking the work on the outside of the body, and it is not necessary to perform connecting work or drawing work which is difficult on the inside of the body. In addition, there is not a case where complicated puncturing work from the inside of the body toward the outside of the body in which special dedicated forceps are used, is performed. Therefore, reduction of installation work time of a camera unit is achieved, and an increase in surgery time for the installation is also prevented. In addition, since the installation work becomes simple, safety is high from the viewpoint of the effects on human mental health without stressing out a practitioner.

In addition, since a wire-like drawing auxiliary tool can have a diameter which is smaller than that of the cable, the needle-like device which is used in puncturing can have an outer diameter which is equivalent to that of the cable. Therefore, it is possible to perform minimally invasive surgery in which a wound of a patient is much smaller.

Therefore, according to one aspect of the present invention, it is possible to provide a camera system for monitoring the inside of a body which can be installed during a short period of time by simple installation work, and a method for installing the camera system for monitoring the inside of a body.

BRIEF DESCRIPTION OF DRAWINGS

FIG. 3(a) is a view of the puncturing device, FIG. 3(b) is a sectional view of FIG. 3(a), FIG. 3(c) is a view of an obturator which is used in puncturing by being combined with the puncturing device, and FIG. 3(d) is a sectional view illustrating a state where the obturator passes through the puncturing device.

FIG. 4(a) is a view of the wire-like drawing auxiliary tool, FIG. 4(b) is a sectional view in which the wire-like drawing auxiliary tool is inserted into the puncturing device, and FIG. 4(c) is a view illustrating a state where a stopper which fixes a wire is added to FIG. 4(b).

FIG. 5(a) is a view illustrating an example of a connection unit of the wire-like drawing auxiliary tool, FIG. 5(b) is a view illustrating a connector unit of a camera cable, FIG. 5(c) is a view illustrating that a camera cable connector unit is connected to a wire-like drawing auxiliary tool connection unit, and FIGS. 5(d) and 5(e) are views respectively illustrating a section taken along line A-A' and a section taken along line B-B' of FIG. 5(c). In addition, FIG. 5(f) is a view illustrating an example of a wire-like drawing auxiliary tool connection unit protection cap, and FIG. 5(g) is a view illustrating a section taken along line C-C' of FIG. 5(f). FIG. 5(h) is a view illustrating a state where the wire-like drawing auxiliary tool connection unit is covered with the connection unit protection cap and is inserted into the puncturing device.

FIG. 12(e) is another example of FIG. 12(d).

FIG. 13(a) is a sectional view illustrating each of sections of the puncturing device used as the camera support tube and the camera unit support tube joining unit illustrated in FIG. 9(a), and FIG. 13(b) is a sectional view illustrating a joined state of the puncturing device used as the camera support tube and the support tube joining unit which are illustrated in FIG. 13(a). FIG. 13(c) is a view illustrating a connected state by adding the camera unit and a camera side cable to FIG. 13(b). FIG. 13(d) is a view illustrating an example in which the puncturing device is fixed to the camera unit by using a cable fastener, and FIG. 13(e) is another example in which the fixing is performed by using a cable fastener.

FIG. 16 is a schematic view illustrating a schematic configuration of a camera system for monitoring the inside of a body according to Embodiment 3.

DESCRIPTION OF EMBODIMENTS

Figure 1:
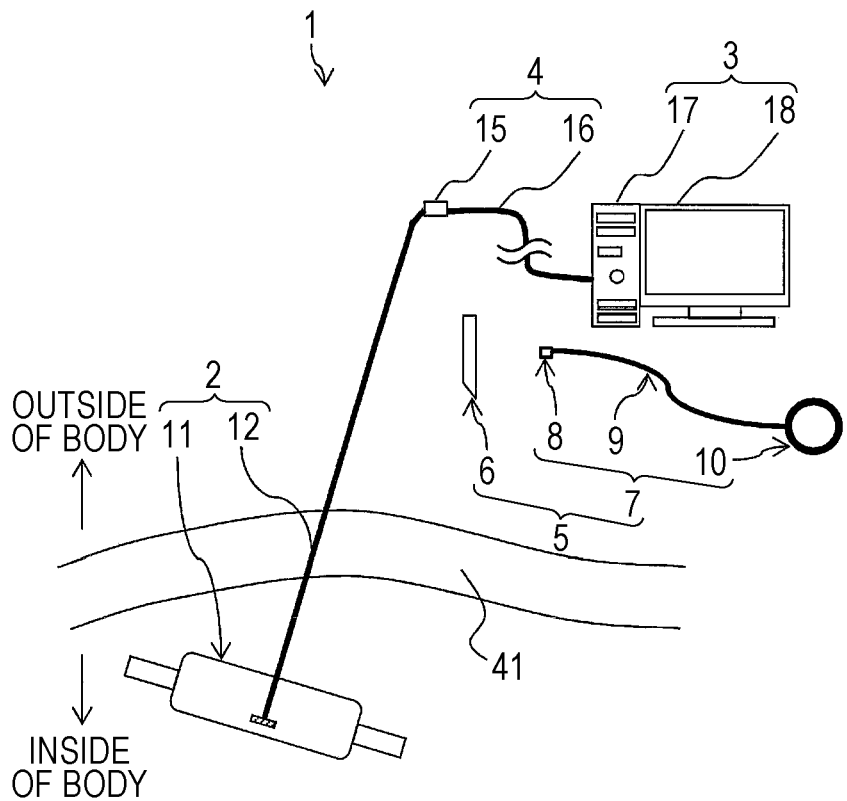
FIG. 1 is a schematic view illustrating a schematic configuration of a camera system for monitoring the inside of a body according to Embodiment 1.
Figure 2:
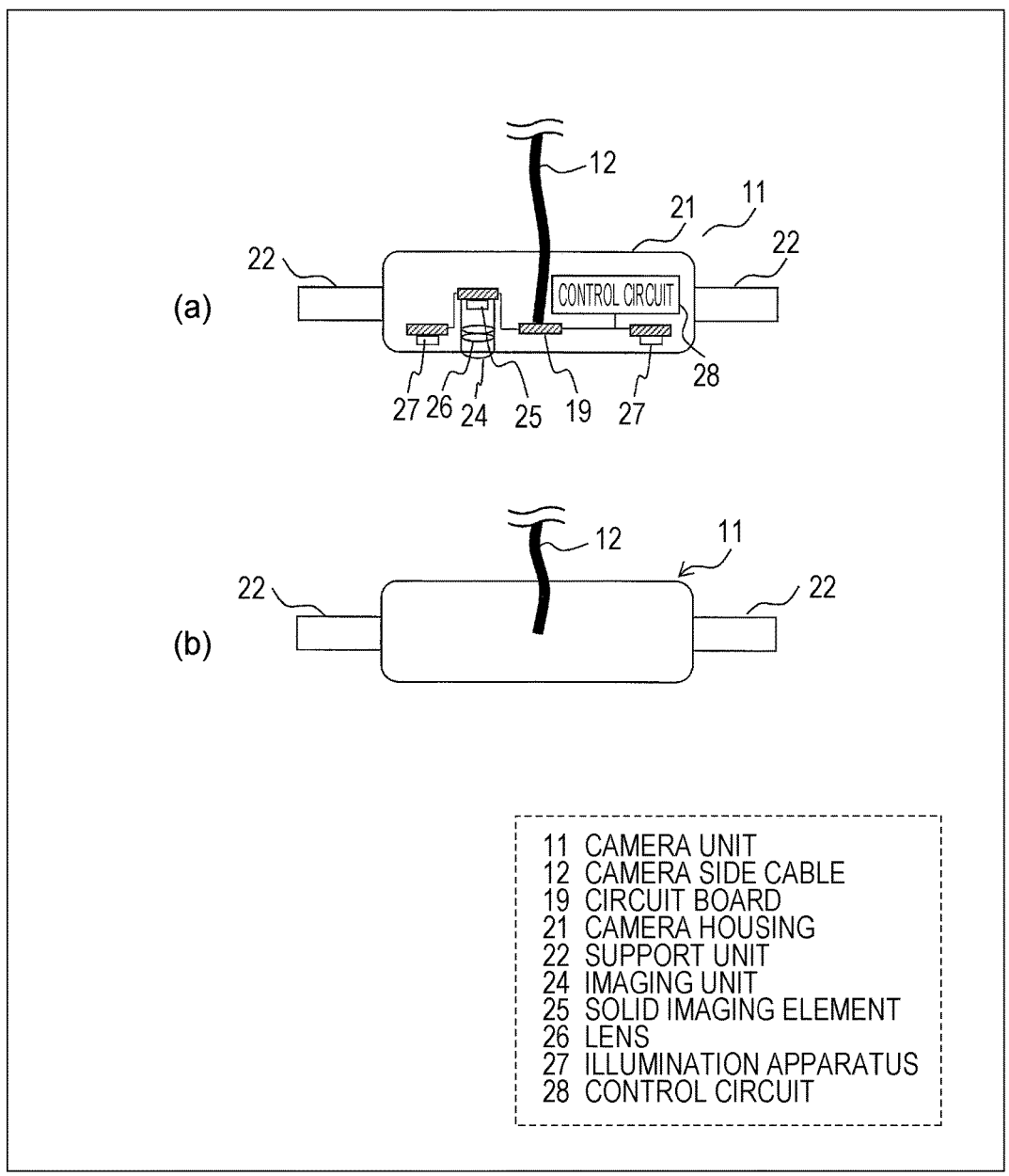
FIG. 2(a) is a sectional view schematically illustrating a schematic configuration of main parts of an imaging apparatus according to Embodiment 1.
FIG. 2(b) is an upper view of the imaging apparatus illustrated in FIG. 2(a).
Figure 3:
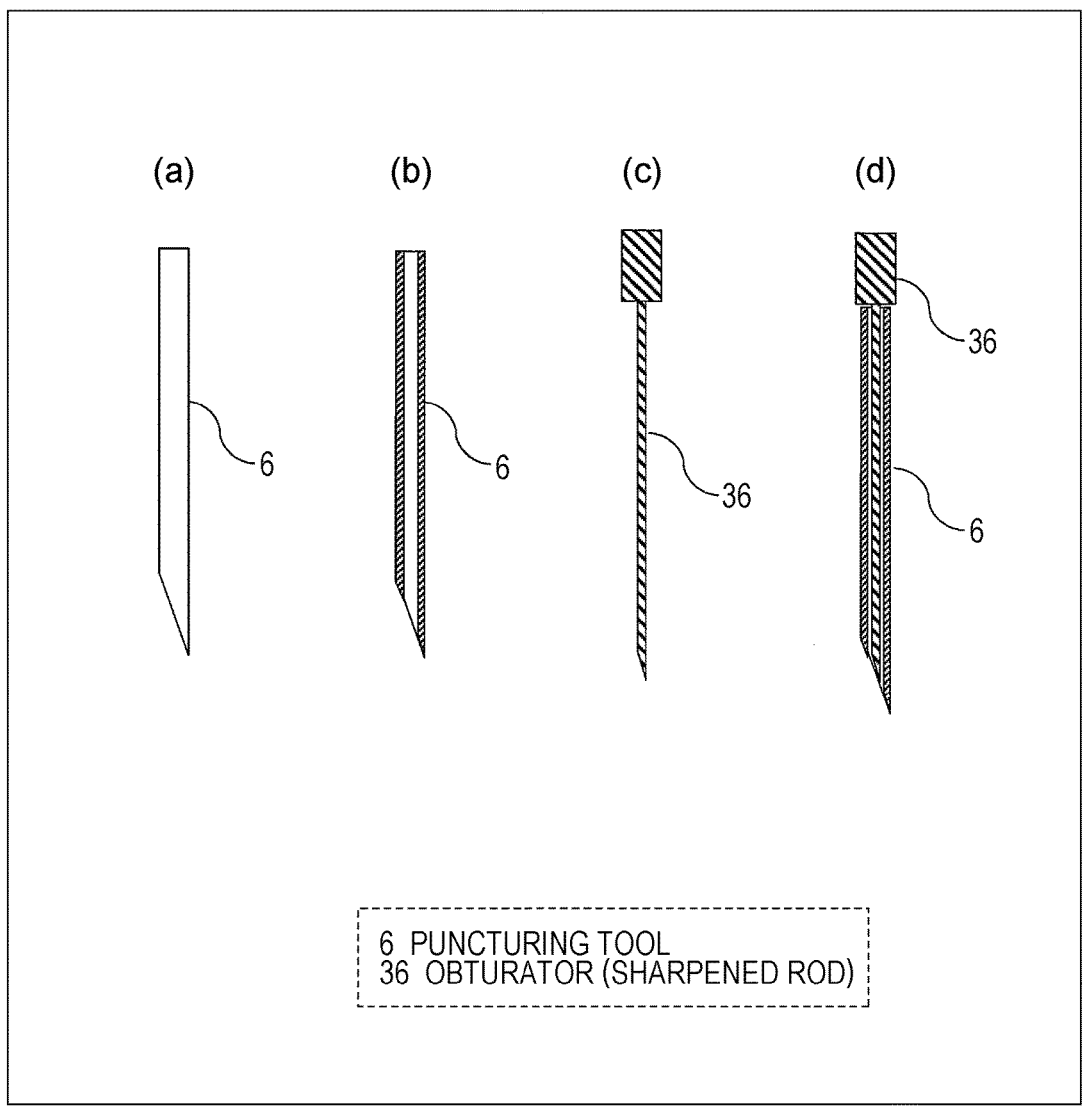
FIGS. 3(a) to 3(d) are views illustrating an example of a puncturing device according to Embodiment 1.
Figure 4:
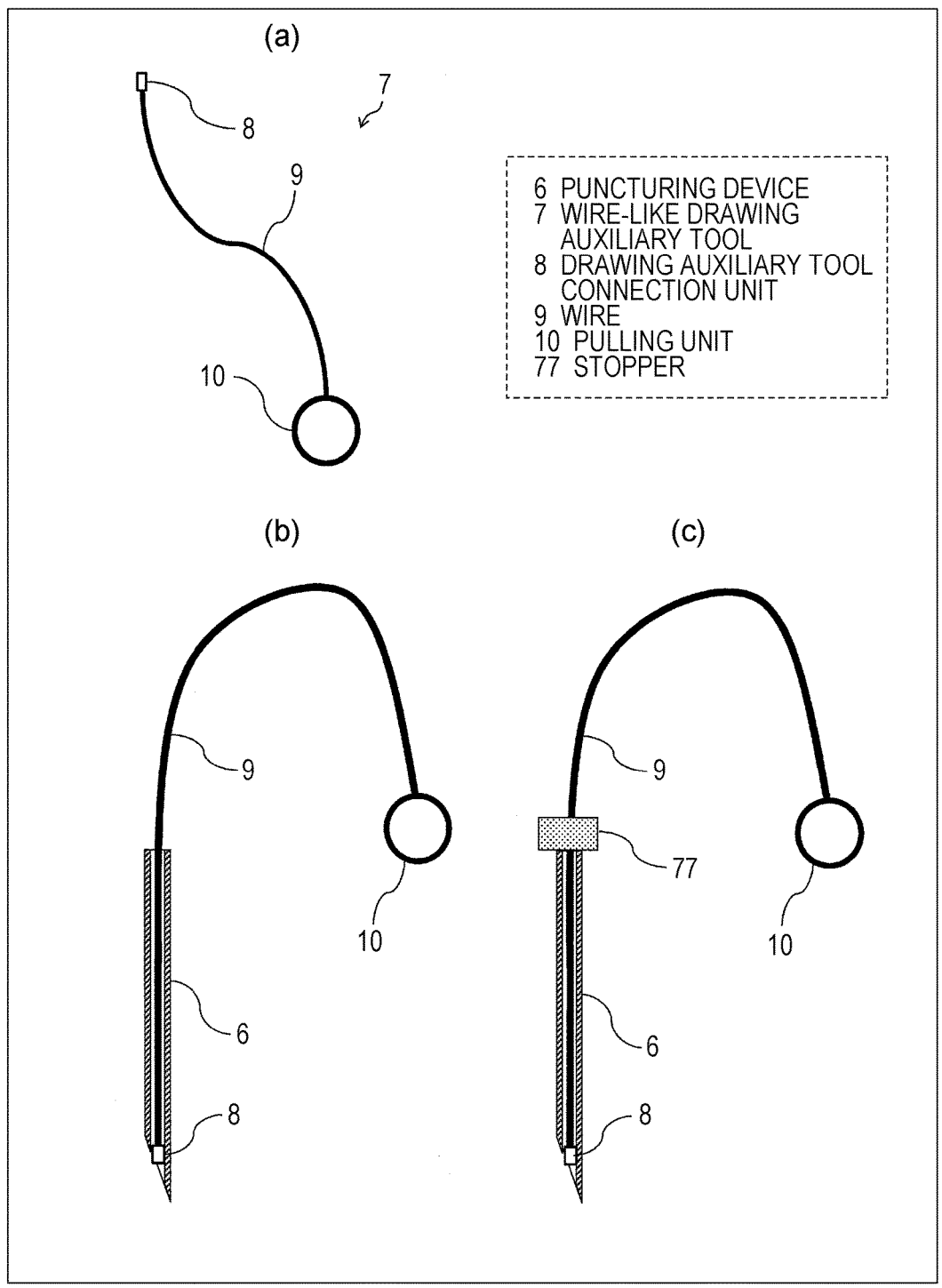
FIGS. 4(a) to 4(c) are views illustrating an example of a wire-like drawing auxiliary tool according to Embodiment 1.
Figure 5:
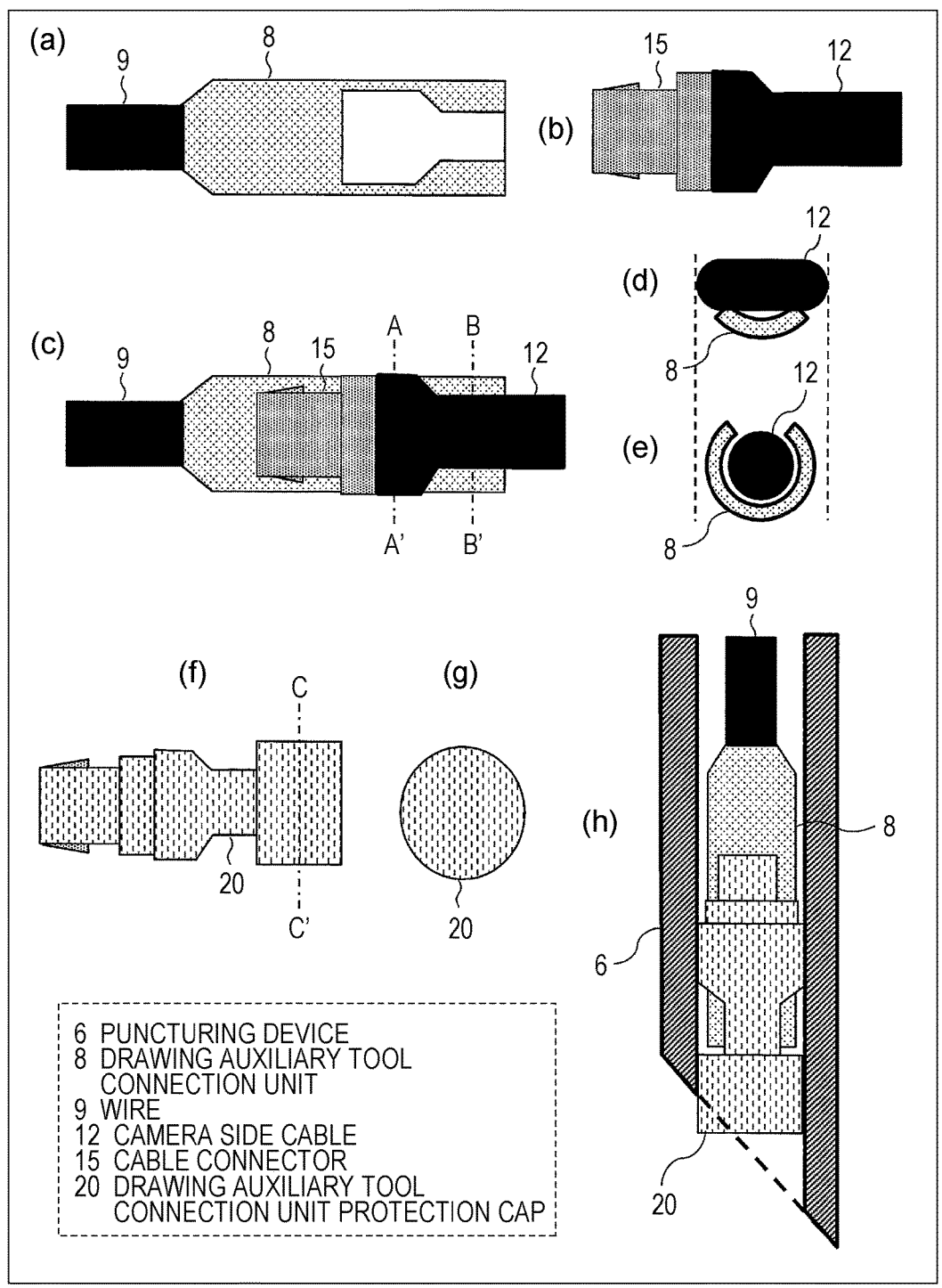
FIGS. 5(a) to 5(h) are views illustrating an example of the wire-like drawing auxiliary tool according to Embodiment 1.
Figure 6:
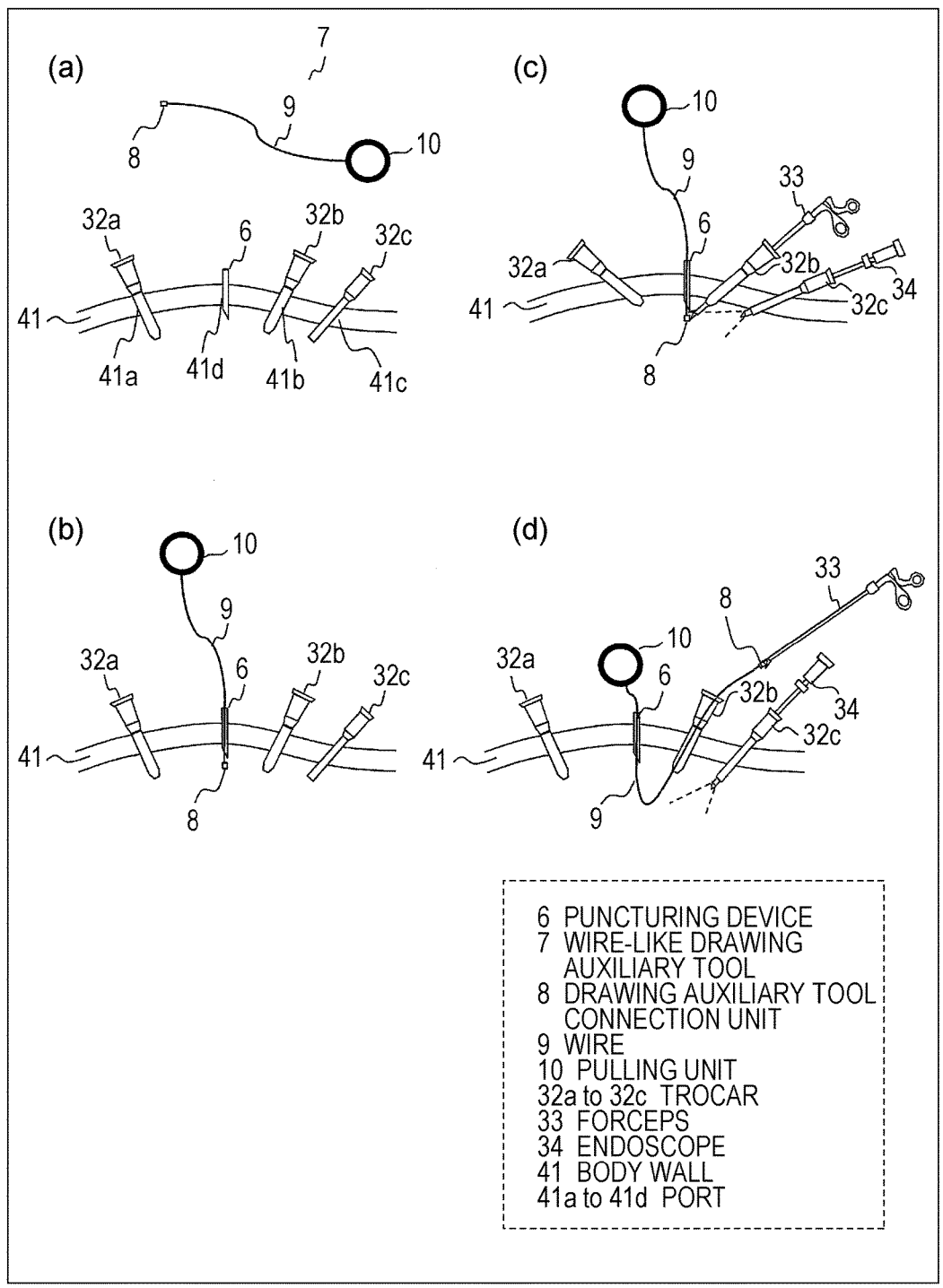
FIGS. 6(a) to 6(d) are schematic views illustrating a method for installing the imaging apparatus in the camera system for monitoring the inside of a body according to Embodiment 1, in a process order.

One embodiment of the present invention will be described based on FIGS. 1 to 7 as follows. In addition, for convenience of the description, members having the same functions as those of members illustrated in each embodiment are given the same reference numerals, and the description thereof will be appropriately omitted. In addition, the shape and the dimensions, such as the length, the size, or the width, of configuration elements described in each drawing do not reflect the real shape or dimensions, and are appropriately changed for clarifying and simplifying the drawings.

Embodiment 1

<Schematic Configuration of Camera System for Monitoring Inside of Body>

FIG. 1 is a schematic view illustrating a schematic configuration of a camera system for monitoring the inside of a body 1 according to the embodiment.

As illustrated in FIG. 1, the camera system for monitoring the inside of a body 1 according to the embodiment is provided with an imaging apparatus 2, a control system 3, a connection unit 4, and a drawing auxiliary tool 5.

Hereinafter, each configuration element will be described in detail.

<Schematic Configuration of Imaging Apparatus 2>

FIG. 2(a) is a sectional view schematically illustrating a schematic configuration of main parts of the imaging apparatus 2 according to the embodiment. FIG. 2(b) is an upper view of the imaging apparatus 2 illustrated in FIG. 2(a).

As illustrated in FIGS. 1, 2(a), and 2(b), the imaging apparatus 2 is provided with a camera unit 11 (imaging part) which captures the inside of the body, and a camera side cable 12 (cable) which is connected to the camera unit 11.

(Camera Unit 11)

As illustrated in FIGS. 2(a) and 2(b), the camera unit 11 is provided with a camera housing 21, a circuit board 19, an imaging unit 24, a control circuit 28, an illumination apparatus 27, and a support unit 22.

The circuit board 19, the imaging unit 24, the control circuit 28, and the illumination apparatus 27 are provided in the camera housing 21. Meanwhile, the support unit 22 is provided on the outer side of the camera housing 21.

First, a configuration of the inside of the camera housing 21 will be described.

The imaging unit 24 is provided with a lens 26 which is an imaging lens, and a solid-state imaging element 25.

The solid-state imaging element 25 is disposed so that an optical axis and an axial center of the lens 26 match each other. Examples of the solid-state imaging element 25 include a charge coupled device (CCD) or a complementary metal-oxide semiconductor (CMOS) image sensors.

The illumination apparatus 27 makes an image captured by the camera unit 11 clear by illuminating the inside of the body. It is preferable that the size of the illumination apparatus 27 is small, and for example, a light emitting diode (LED) or the like can be appropriately used. In addition, in the camera unit 11, only one illumination apparatus 27 may be provided, or a plurality of illumination apparatuses 27 may be provided as illustrated in FIG. 2(a).

The solid-state imaging element 25, the illumination apparatus 27, and the control circuit 28 are connected to the circuit board 19.

The control circuit 28 is electrically connected to the imaging unit 24 and the illumination apparatus 27 via the circuit board 19.

In addition, one end part of the camera side cable 12 is connected to the circuit board 19, and a signal is input and output between the circuit board 19 and a camera unit control equipment 17 (refer to FIG. 1) in the control system 3 via the camera side cable 12 and the connection unit 4 (refer to FIG. 1).

Accordingly, the control circuit 28 controls the driving of the imaging unit 24 and the illumination apparatus 27 based on a control signal input from the camera unit control equipment 17 via the camera side cable 12 and the circuit board 19.

Next, the camera housing 21 and the support unit 22 which is provided on the outside of the camera housing 21 will be described.

The support unit 22 is provided to protrude outward from each of both side surfaces which oppose each other in the camera housing 21.

The support unit 22 is used as a gripping unit in the camera unit 11. The camera unit 11 passes through, for example, a trocar 32 (tube-like member, refer to FIG. 6), and is guided toward the inside of the body. The support unit 22 is for supporting the camera unit 11. When the camera unit 11 is guided toward the inside of the body from the trocar 32 by using forceps, when the camera unit is taken out of the support tube after being used, or when the camera unit is collected from the trocar, the support unit 22 is gripped, and can support the camera unit 11.

(Camera Side Cable 12)

The camera side cable 12 is a communication cable on a camera side. The camera side cable 12 sends the image captured by the camera unit 11 to the camera unit control equipment 17 via the connection unit 4 as an image signal, or sends the control signal from the camera unit control equipment 17 to the camera unit 11.

The camera side cable 12 is connected to the circuit board 19, and is guided toward the outside of the camera unit 11. In addition, the connection unit of the circuit board 19 and the camera side cable 12 is sealed by a resin or the like which is not illustrated.

The camera side cable 12 passes through the trocar 32 (refer to FIG. 6) or the like in a state of being connected to the camera unit 11 and is guided toward the inside of a body cavity, or passes through a puncturing device 6 (refer to FIG. 3) which will be described later and is drawn out toward the outside of the body. Therefore, the camera side cable 12 is formed of a flexible material having ductility.

<Control System 3>

As illustrated in FIG. 1, the control system 3 is provided with the camera unit control equipment 17 and a display 18 (display apparatus).

The camera unit control equipment 17 displays the image sent from the camera unit 11 on the display 18. In addition, the camera unit control equipment 17 sends the control signal to the camera unit 11. In addition, the camera unit control equipment 17 and the display 18 may be integrated with each other, or may be configured as separate bodies.

<Connection Unit 4>

As illustrated in FIG. 1, the connection unit 4 is a connection unit which connects the camera side cable 12 and the camera unit control equipment 17 to each other. The connection unit 4 is provided with an equipment side cable 16 and a cable connector 15 which links the equipment side cable 16 and the camera side cable 12 to each other.

Therefore, the camera unit 11 is connected to the camera unit control equipment 17 via the camera side cable 12, the cable connector 15 linked to the camera side cable 12, and the equipment side cable 16.

Accordingly, via the camera side cable 12 and the equipment side cable 16, the image captured by the camera unit 11 is sent to the camera unit control equipment 17, and the control signal from the camera unit control equipment 17 is sent to the camera unit 11.

<Schematic Configuration of Drawing Auxiliary Tool 5>

The camera system for monitoring the inside of a body 1 according to the embodiment is provided with a wire-like drawing auxiliary tool 7 (auxiliary device having a wire structure) as the drawing auxiliary tool 5 for drawing out the camera side cable 12 toward the outside of the body, and the needle-like puncturing device 6.

(Puncturing Device 6)

Here, a structure of the puncturing device 6 will be described with reference to FIGS. 3(a) to 3(d) in more detail.

FIG. 3(a) is a view illustrating an example of the puncturing device 6 according to the embodiment, FIG. 3(b) is a sectional view of FIG. 3(a), FIG. 3(c) is a view of an obturator (sharpened rod) which is used in puncturing by being combined with the puncturing device, and FIG. 3(d) is a sectional view illustrating a state where the obturator passes through the puncturing device. In general, the puncturing device, such as the trocar, has a sharp tip end, has a pipe-like hollow structure having a cavity on the inside thereof, and is used by passing through and being combined with the obturator 36 when puncturing is performed. Hereinafter, an example of the puncturing device having the tip end similar to an injection needle.

(Wire-Like Drawing Auxiliary Tool)

FIG. 4(a) is a sectional view illustrating a schematic configuration of the wire-like drawing auxiliary tool which is used in the embodiment, FIG. 4(b) is a sectional view in which the wire-like drawing auxiliary tool is inserted into the puncturing device, and FIG. 4(c) is a view illustrating a state where a stopper which fixes wire is added to FIG. 4(b). In addition, FIG. 5(a) is a view illustrating an example of a connection unit of the wire-like drawing auxiliary tool, FIG. 5(b) is a view illustrating a connector unit of a camera cable, FIG. 5(c) is a view illustrating that a camera cable connector unit is connected to a wire-like drawing auxiliary tool connection unit, and FIGS. 5(d) and 5(e) are respectively a view illustrating a section taken along line A-A' and a section taken along line B-B' of FIG. 5(c). In addition, FIG. 5(f) is a view illustrating an example of a wire-like drawing auxiliary tool connection unit protection cap, and FIG. 5(g) is a view illustrating a section taken along line C-C' of FIG. 5(f). FIG. 5(h) is a view illustrating a state where the wire-like drawing auxiliary tool connection unit is covered with the connection unit protection cap and is inserted into the puncturing device.

As illustrated in FIG. 4(a), the wire-like drawing auxiliary tool 7 which is used in the embodiment is configured of a connection unit 8 and a wire unit 9 for being joined to the cable provided at the end part, and the pulling unit 10 provided at the other end part. In addition, as illustrated in FIG. 4(b), the wire-like drawing auxiliary tool 7 is a wire-like device in which the outer diameters of the wire unit 9 and the connection unit 8 are smaller than the inner diameter of the needle-like puncturing device 6. In addition, the pulling unit 10 has dimensions which is sufficiently greater than the inner diameter of the puncturing device.

FIG. 5(a) is a view illustrating an example of the connection unit 8 of the drawing auxiliary tool. The connection unit 8 of the drawing auxiliary tool has a structure in which the connection unit 8 also serves as a waterproof cap of the cable connector 15 as illustrated in FIG. 5(b), has a recessed shape which corresponds to the shape of the cable connector 15 illustrated in FIG. 5(c), and is connected to be fitted to this part. FIG. 5(d) is a section taken along line A-A' of FIG. 5(c), FIG. 5(e) is a section taken along line B-B', and illustrates a structure which is hooked and fastened by using a neck of the cable connector 15 therebetween, and which does not fall out even when being pulled. In this manner, the connection unit 8 of the drawing auxiliary tool has a shape which can fix the cable connector 15.

In order to make the inner diameter of the puncturing device 6 as small as possible, the width of the connection unit 8 of the drawing auxiliary tool illustrated in FIG. 5(e) becomes equal to or smaller than the width of the cable connector 15 illustrated in FIG. 5(d).

FIG. 5(f) is a protection cap (connection unit protection cap) of the drawing auxiliary tool connection unit for preventing dust from infiltrating and adhering to the inside of the connection unit 8 of the drawing auxiliary tool when passing through the inside of the body, and the protection cap is set again when being guided in, and is taken out when connecting the cable connector. A protection cap 20 has a shape which matches the shape of the cable connector, but on the section taken along line C-C' of FIG. 5(f) illustrated in FIG. 5(g), the protection cap 20 has a cylindrical shape which matches the shape of the tube unit of the puncturing device 6. In other words, the protection cap 20 includes a part which corresponds to the shape of the cable connector 15, and a cylindrical shape which corresponds to the shape of the inside of the puncturing device 6.

Therefore, the wire-like drawing auxiliary tool 7 can be guided toward the inside of an opening unit which is opened in a shape of a tube in the needle-like puncturing device 6.

In general, the puncturing is performed using the obturator 36, but instead of the obturator 36, it is possible to use the wire-like drawing auxiliary tool 7. As illustrated in FIG. 5(h), a structure in which liquid is prevented from entering the inside of the tube of the puncturing device 6 even in a case where the puncturing device 6 is inserted into a body wall 41 in a state where the wire-like drawing auxiliary tool 7 is guided toward the inside of the puncturing device 6, is achieved. In addition, as illustrated in FIG. 4(c), when the wire unit 9 is configured of a shrink-proof material in the axial direction, it is possible to fix the connection unit 8 to the tip end of the puncturing device 6 by fixing the wire by a stopper 77.

Accordingly, there is not a case where the tube is clogged with the liquid when the needle-like puncturing device enters the inside of the body, and the end part of the wire-like drawing auxiliary tool which has entered the needle-like puncturing device can penetrate the body wall 41, and can be guided toward the inside of the body. In addition, since the obturator 36 is not used, it is possible to further simplify the puncturing work.

In addition, it is preferable that the diameter of the puncturing device 6 is small in order to realize minimal invasiveness. Specifically, it is preferable that the diameter is equal to or less than 3 mm.

<Method for Installing Camera System for Monitoring Inside of Body 1>

Next, both a method for installing the imaging apparatus 2 in the camera system for monitoring the inside of a body 1 according to the embodiment, and a method of use thereof, will be described.

FIGS. 6(a) to 6(d) and FIGS. 7(a) to 7(d) are schematic views illustrating the method for installing the imaging apparatus 2 in the camera system for monitoring the inside of a body 1 according to the embodiment, in a process order.

As illustrated in FIG. 6(a), first, the practitioner opens ports 41a to 41c (holes) for inserting the forceps or the endoscope into the body cavity on the body wall 41, and inserts each of the plural trocars 32 (hereinafter, referred to as trocars 32a to 32c) into the ports 41a to 41c.

Furthermore, in order to install the camera unit 11 inside the body cavity, a port 41d is opened at a position where the entire organ including an affected part can be seen on the body wall 41, and the puncturing device 6 is inserted.

Specifically, by puncturing the obturator into the port in a state where the needle-like obturator (not illustrated) has passed through the inside of the puncturing device 6, the puncturing device 6 is inserted into the body wall 41.

Instead of the obturator, the wire-like drawing auxiliary tool 7 may be inserted again.

After the trocars 32a to 32c and the puncturing device 6 are inserted into the body wall 41, the practitioner sends gas into the body through at least one trocar among the trocars 32a to 32c, and expands the inside of the body cavity.

Next, as illustrated in FIG. 6(b) the wire-like drawing auxiliary tool 7 is inserted, and the connection unit 8 is out of the tip end of the puncturing device 6.

As illustrated in FIG. 6(c), the practitioner inserts an endoscope 34 into the body cavity through the trocar 32c, and grips the connection unit 8 by forceps 33 while observing the inside of the body using the endoscope 34, and as illustrated in FIG. 6(d), the connection unit 8 and the wire unit 9 are drawn out toward the outside of the body from the trocar 32b. Since the pulling unit 10 is present at the other one end, the wire is not mistakenly dropped on the inside of the body, and the operation can be safely performed.

Next, as illustrated in FIG. 7(a), the camera side cable 12 is connected to the connection unit 8 as illustrated in FIG. 5(c).

Next, as illustrated in FIG. 7(b), while pulling the pulling unit 10, the camera unit 11 is gripped by the forceps 33, and the trocar 32b is inserted into the body cavity through the trocar 32b.

Next, as illustrated in FIG. 7(c), while further pulling the pulling unit 10, and extracting the puncturing device 6 from the body wall 41, the camera unit 11 is pulled up to an installation position of the body wall, and is fixed by using a cable fastener 43.

Since the puncturing device 6 is extracted and only the camera side cable 12 remains, the outer diameter of the puncturing device 6 can be equivalent to that of the camera side cable 12, and for example, can be 2 mm. The diameter of the cable connector 15 (connection unit 8) slightly increases to be approximately 3 mm, but since the area is small, the body wall 41 can pass through the hole of the body wall while temporarily widening the hole. Therefore, the affected part of an installation unit of the camera unit 11 can be the minimum, and more minimal invasiveness can be achieved.

Next, as illustrated in FIG. 7(d), the wire-like drawing auxiliary tool 7 is removed, the camera side cable 12 and an extending cable 16a are connected to each other by the cable connector 15, and the extending cable 16a and the equipment side cable 16 are connected to each other by a cable connector 15a. Furthermore, since the extending cable or the equipment side cable do not pass through the inside of the body, the cable having a large diameter can be used.

Accordingly, the entire image of the inside of the body captured by the camera unit 11 is displayed on the display 18 by the camera unit control equipment 17.

Next, while seeing the image of the display 18 and the image of the camera unit 11 reflected by the endoscope 34, the support unit 22 is gripped by the forceps 33, the camera unit 11 is moved, and the orientation inside the body cavity is adjusted.

In a case where the camera image is seen not from immediately above but diagonally at a certain angle, a camera unit in which a drawing position of the cable of the camera unit is deviated in the diagonal direction from an optical axis of the camera, may be prepared in advance. After the positioning of the camera unit is completed, by using the cable fastener 43, the camera unit is then fixed to the body wall, and is started to be used.

Accordingly, the practitioner can perform treatment using the forceps while enlarging and observing the work region (local region) on the display of the endoscope, and can also grasp the state (movement of the forceps or the like, a bleeding site, and a residual, such as gauze, outside the work region) outside the work region on the display 18.

In PTL 2, a hook needle is used for installing the camera inside of the body, but since the hook needle has a shape of a rod, it is necessary to perform an operation of hooking the communication cable to a hook unit of the hook needle, and it is not easy to draw out the communication cable toward the outside of the body.

Meanwhile, since the drawing auxiliary tool 7 of the embodiment has the wire structure, as illustrated in FIGS. 6(c) and 6(d), the connection unit 8 of the wire-like drawing auxiliary tool 7 can be pulled into the inside of the body via the puncturing device 6, and can be drawn out toward the inside of the body via the trocar 32b.

Therefore, as illustrated in FIG. 7(a), the camera side cable 12 is connected to the connection unit 8 on the outside of the body, and as illustrated in FIGS. 7(b) and 7(c), by pulling the pulling unit 10, the camera unit 11 is pulled into the inside of the body, and further, the end part of the camera side cable 12 can be drawn out toward the outside of the body, and can be electrically connected to the control system 3. Accordingly, it is possible to install the camera on the inside of the body by a simple method.

<Method for Collecting Camera Unit 11>

An order of collecting the camera unit 11 after the surgery is finished, will be described.

First, the cable connector 15 and the cable fastener 43 are removed, and the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out a cut organ.

<Effect>

As described above, according to the embodiment, during the endoscopic surgery, it is possible to install an apparatus which can grasp a situation on the inside of the body in a wide viewing field and can substantially enhance safety, during a short period of time without stressing out a practitioner by a simple and safe method only by generating a minimal wound which is equivalent to the size of the outer diameter of the camera side cable 12.

Embodiment 2

Another embodiment of the present invention will be described based on FIGS. 8 to 15 as follows. In addition, mainly, differences from Embodiment 1 will be described, configuration elements which have the same functions as those of the configuration elements used in Embodiment 1 will be given the same reference numerals, and the description thereof will be omitted. In addition, in the embodiment, it is also needless to say modifications similar to those of Embodiment 1 are possible.

<Schematic Configuration of Camera System for Monitoring Inside of Body]

Figure 8:
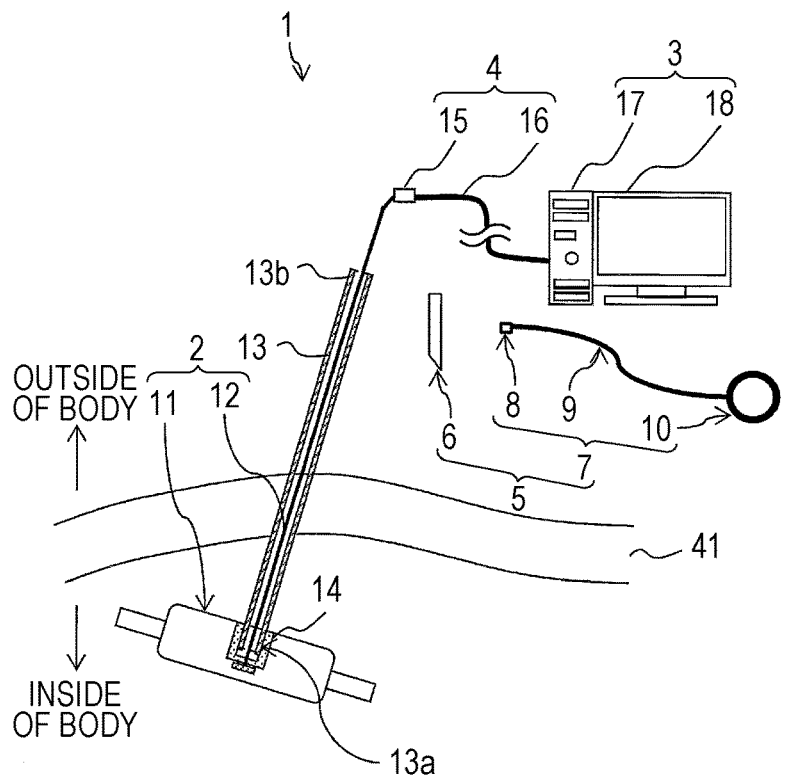
FIG. 8 is a schematic view illustrating a schematic configuration of a camera system for monitoring the inside of a body according to Embodiment 2.

FIG. 8 is a schematic view illustrating a schematic configuration of the camera system for monitoring the inside of a body 1 according to the embodiment.

As illustrated in FIG. 8, the camera system for monitoring the inside of a body 1 according to the embodiment is provided with the imaging apparatus 2, a camera support tube 13 (support tube), the control system 3, the connection unit 4, and the drawing auxiliary tool 5.

Hereinafter, each configuration element will be described in detail. Description of the control system 3, the connection unit 4, and the drawing auxiliary tool 5 will be omitted since the control system 3, the connection unit 4, and the drawing auxiliary tool 5 are the same as those of Embodiment 1.

<Schematic Configuration of Imaging Apparatus 2>

FIG. 9(a) is a sectional view schematically illustrating a schematic configuration of main parts of the imaging apparatus 2 according to the embodiment, and FIG. 9(b) is an upper view of the imaging apparatus 2 illustrated in FIG. 9(a).

As illustrated in FIGS. 8 and 9(a) and 9(b), the imaging apparatus 2 is provided with the camera unit 11 (imaging part) which captures the inside of the body, and the camera side cable 12 (cable) which is connected to the camera unit 11.

(Camera Unit 11)

As illustrated in FIGS. 9(a) and 9(b), the camera unit 11 is provided with the camera housing 21, the circuit board 19, the imaging unit 24, the control circuit 28, the illumination apparatus 27, and the support unit 22.

The circuit board 19, the imaging unit 24, the control circuit 28, and the illumination apparatus 27 are provided in the camera housing 21. Meanwhile, the support unit 22 is provided on the outer side of the camera housing 21.

Since configuration elements except a support tube joining unit 14 are the same as those of Embodiment 1, the description thereof will be omitted.

The camera housing 21 includes a recessed support tube joining unit 14 (joining unit) on an upper surface thereof. The support tube joining unit 14 has an annular opening shape (hole structure) when viewed from above as illustrated in FIG. 9(b), and has a configuration in which a locking female screw 23 is provided on an inner wall of the opening as illustrated in FIG. 9(a). The support tube joining unit 14 may be configured to be fixed at a separate part having not a shape of a screw, but a shape only of being inserted. In addition, it is possible to use the needle-like puncturing device as it is as a support tube, and a recessed shape which corresponds to a shape of the puncturing device may be provided.

(Camera Side Cable 12)

The camera side cable 12 is a camera side communication cable. The camera side cable 12 sends the image captured by the camera unit 11 to the camera unit control equipment 17 via the connection unit 4 as the image signal, or sends the control signal from the camera unit control equipment 17 to the camera unit 11.

The camera side cable 12 is connected to the circuit board 19, and is guided toward the outside of the camera unit 11 to pass through the inside of the support tube joining unit 14. In addition, the connection unit of the circuit board 19 and the camera side cable 12 is sealed by a resin or the like which is not illustrated.

The camera side cable 12 passes through the trocar 32 (refer to FIG. 11) or the like in a state of being connected to the camera unit 11 and is guided toward the inside of the body cavity, or passes through the camera support tube 13 (refer to FIGS. 8 and 10), which is joined to the camera unit 11 via the support tube joining unit 14 and will be described later, and the puncturing device 6 (refer to FIG. 3) and is drawn out toward the outside of the body. Therefore, the camera side cable 12 is formed of a flexible material having ductility.

<Schematic Configuration of Camera Support Tube 13>

As illustrated in FIG. 8, the camera support tube 13 is a support tube which supports the camera unit 11 as being joined to the camera unit 11 on the inside of the body in a state where the camera side cable 12 passes through the inside thereof, and is drawn out toward the outside of the body.

From the viewpoint of the joining strength with the camera unit 11, the camera support tube 13 is formed of a hard material. The material of the camera support tube 13 is not particularly limited if the material has rigidity which makes it possible to obtain the joining strength that can stably support the camera unit 11, and which makes it possible to fix the camera unit 11 at a desirable position and orientation. For example, stainless steel, ceramics (fine ceramics), or reinforced plastic may be used.

One end part 13*a* (first end part) of the camera support tube 13 is guided toward the inside of the body through the body wall 41, such as an abdominal wall. At this time, one end part 13*a* of the camera support tube 13 may be directly guided toward the inside of the body. In addition, the needle-like puncturing device 6 which is used in puncturing may be used as it is as the camera support tube 13. A method of use of the puncturing device 6 as the camera support tube 13 will be described in a modification example 2.

The end part 13*a* guided toward the inside of the body joins with the camera unit 11 by the support tube joining unit 14.

Here, a structure of the camera support tube 13 will be described in more detail with reference to FIGS. 10(*a*) to 10(*c*).

Figure 9:
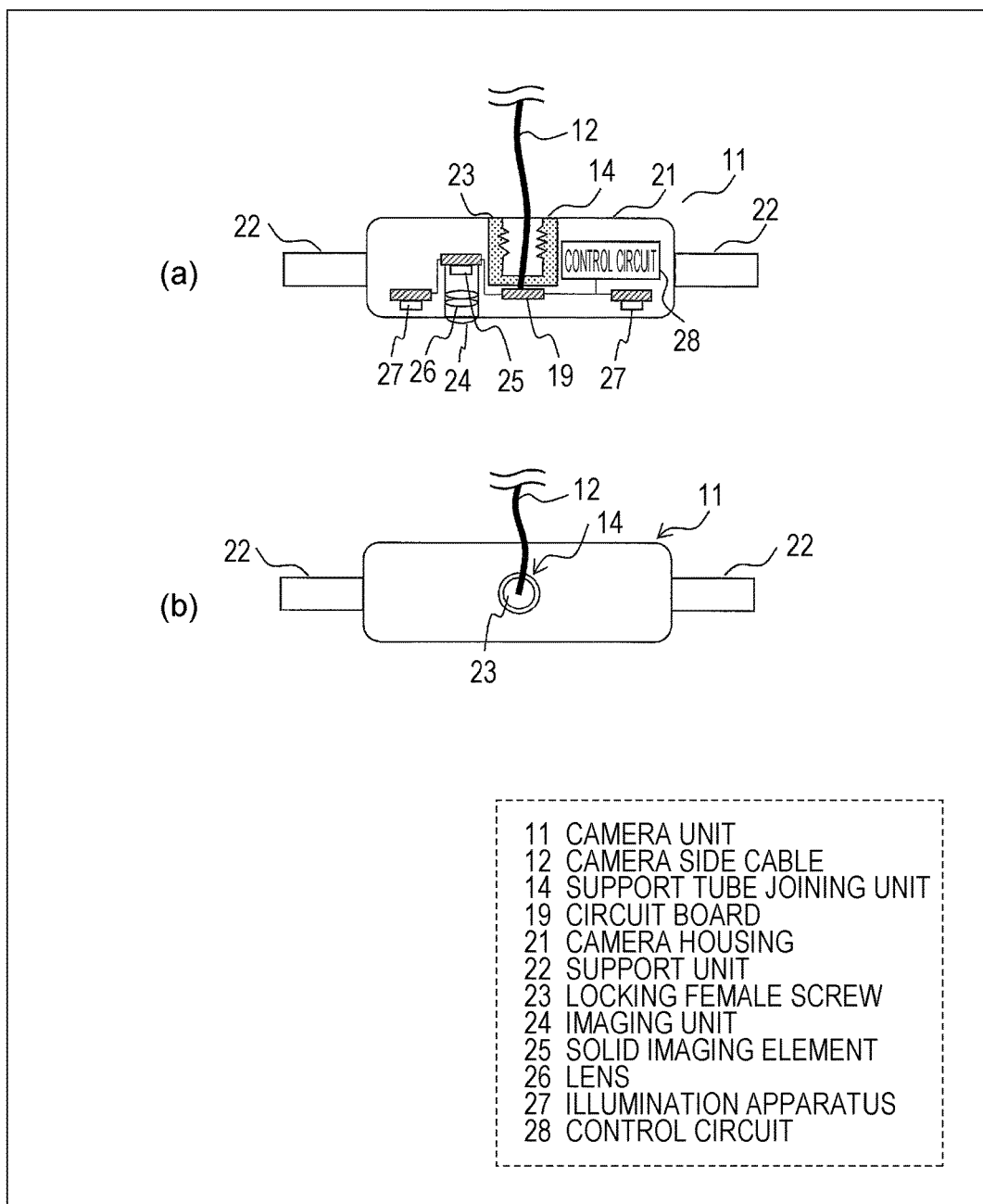
FIG. 9(a) is a sectional view schematically illustrating a schematic configuration of main parts of an imaging apparatus according to Embodiment 2.
FIG. 9(b) is an upper view of the imaging apparatus illustrated in FIG. 9(a).
Figure 10:
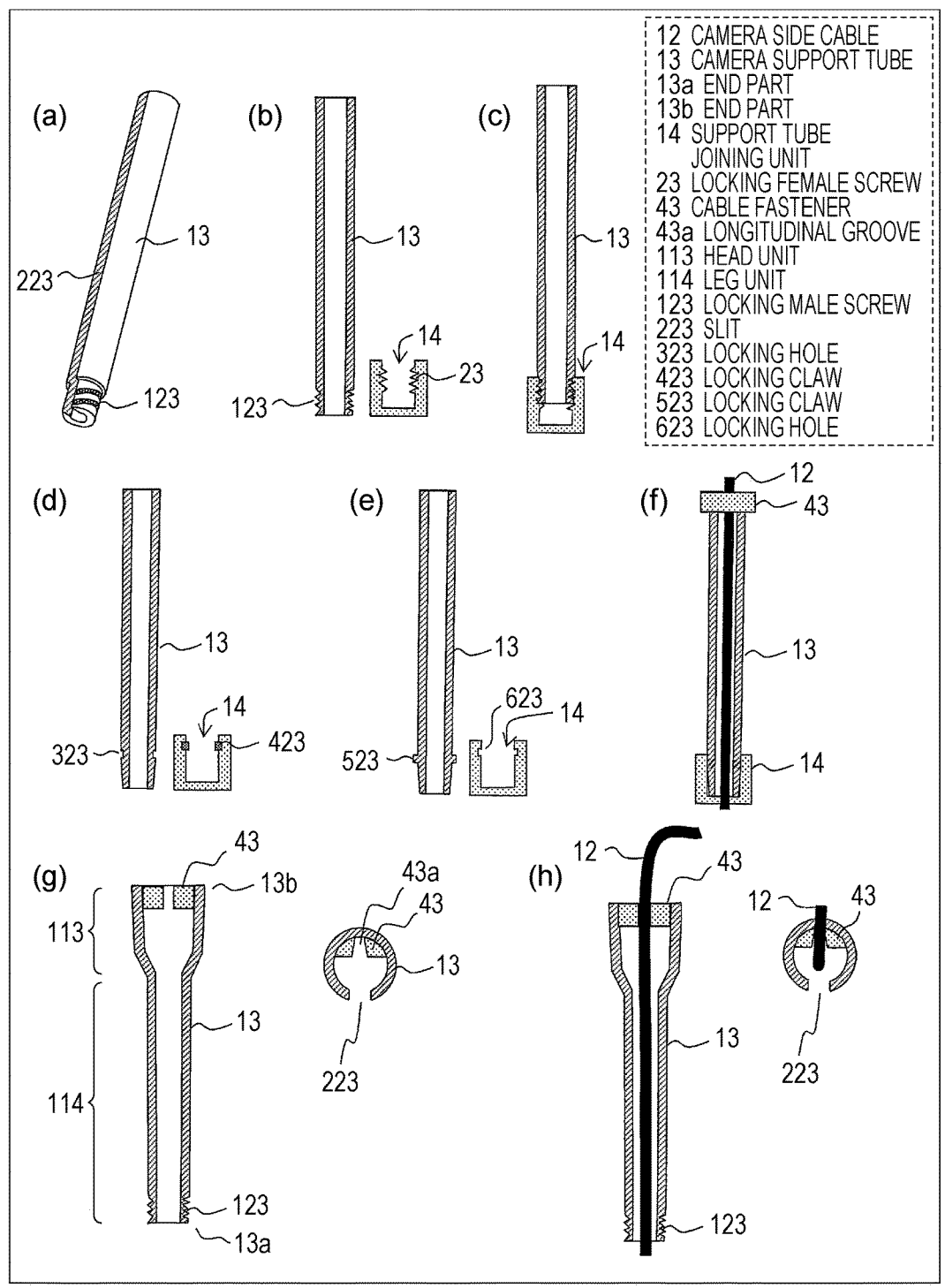
FIG. 10(a) is a perspective view illustrating an example of a camera support tube according to Embodiment 2.
FIG. 10(b) is a sectional view illustrating each of sections of the camera support tube illustrated in FIG. 10(a) and a support tube joining unit illustrated in FIG. 9(a)
FIG. 10(c) is a sectional view illustrating a joined state of the camera support tube and the support tube joining unit which are illustrated in FIG. 10(b). In addition.
FIGS. 10(d) to 10(g) are sectional views illustrating another example of the support tube.
FIG. 10(h) is a sectional view illustrating a state where the camera cable is inserted in FIG. 10(g).

FIG. 10(*a*) is a perspective view illustrating an example of the camera support tube 13 according to the embodiment, FIG. 10(*b*) is a sectional view illustrating each of sections of the camera support tube 13 illustrated in FIG. 10(*a*) and the support tube joining unit 14 illustrated in FIG. 9(*a*), and FIG. 10(*c*) is a sectional view illustrating a joined state of the camera support tube 13 and the support tube joining unit 14 which are illustrated in FIG. 10(*b*). In addition, in FIG. 10(*c*), the camera side cable 12 is omitted.

As illustrated in FIG. 10(*a*), the camera support tube 13 preferably has a cylindrical tube structure. As the camera support tube 13 has a cylindrical shape, as will be described in Embodiment 3 later, it is easy to combine the camera support tube 13 with a general cannula which is the same cylindrical tube.

One end part 13*a* (inside of the body) of the camera support tube 13 and the camera unit 11 on the inside of the body join with each other by the support tube joining unit 14 (joining unit).

As illustrated in FIGS. 10(*a*) to 10(*c*), the camera support tube 13 includes a locking male screw 123 which is screwed (screw-fitted) to the locking female screw 23 provided in the support tube joining unit 14, at the end part 13*a* on a side which is guided toward the inside of the body.

As the locking male screw 123 of the camera support tube 13 is screwed to the locking female screw 23 of the support tube joining unit 14 in this manner, it is possible to join the camera unit 11 and the camera support tube 13 to each other with high mechanical strength.

In addition, as illustrated in FIG. 10(*a*), it is desirable that a slit 223 is provided on a side surface of the camera support tube 13. An advantage of a case where the slit 223 is provided on the side surface of the camera support tube 13 will be described later.

<Method for Installing Camera System for Monitoring Inside of Body 1>

Next, both the method for installing the imaging apparatus 2 in the camera system for monitoring the inside of a body 1 according to the embodiment, and a method of use thereof, will be described.

Figure 11:
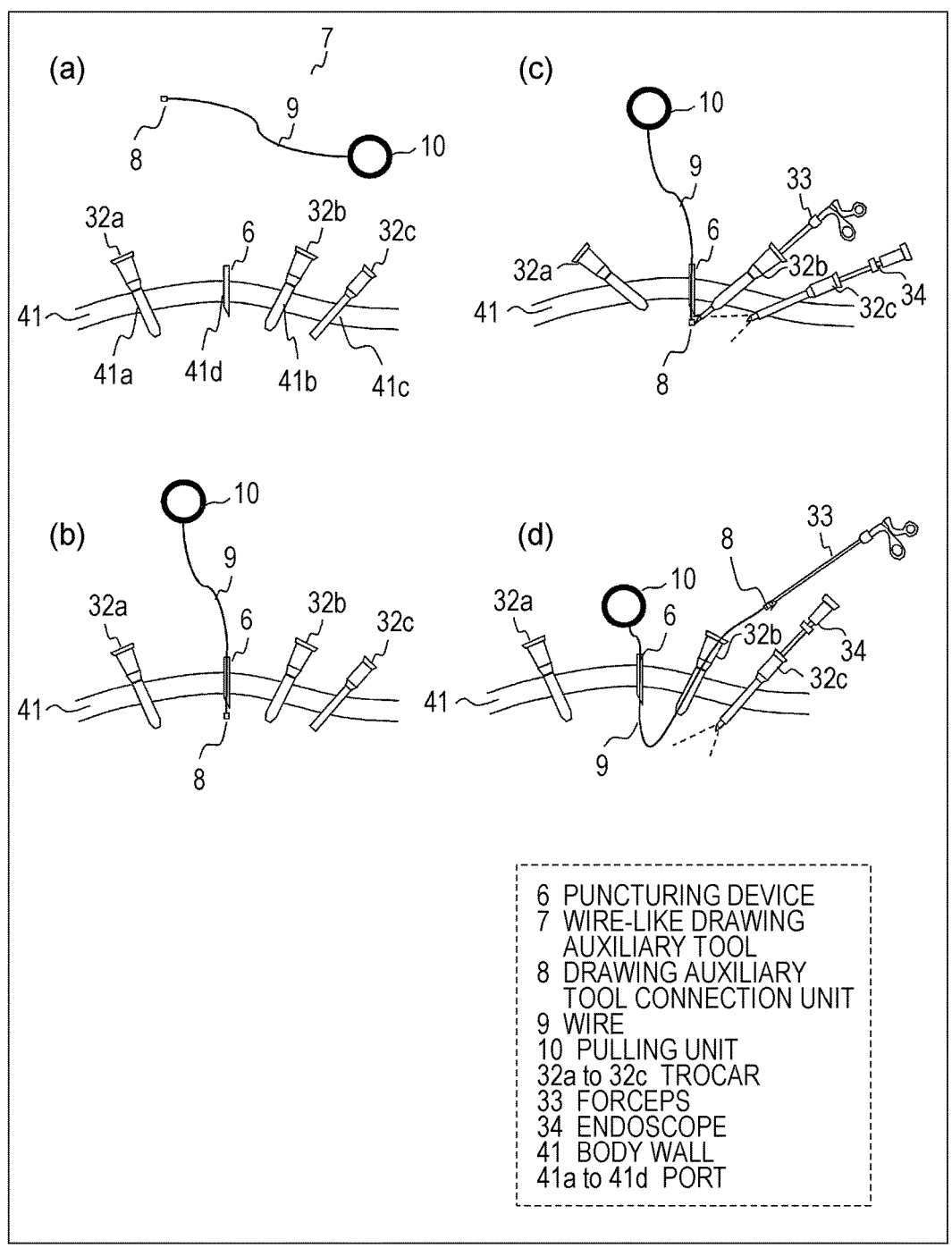
FIGS. 11(a) to 11(d) are schematic views illustrating a method for installing the imaging apparatus in the camera system for monitoring the inside of a body according to Embodiment 2, in a process order.
Figure 12:
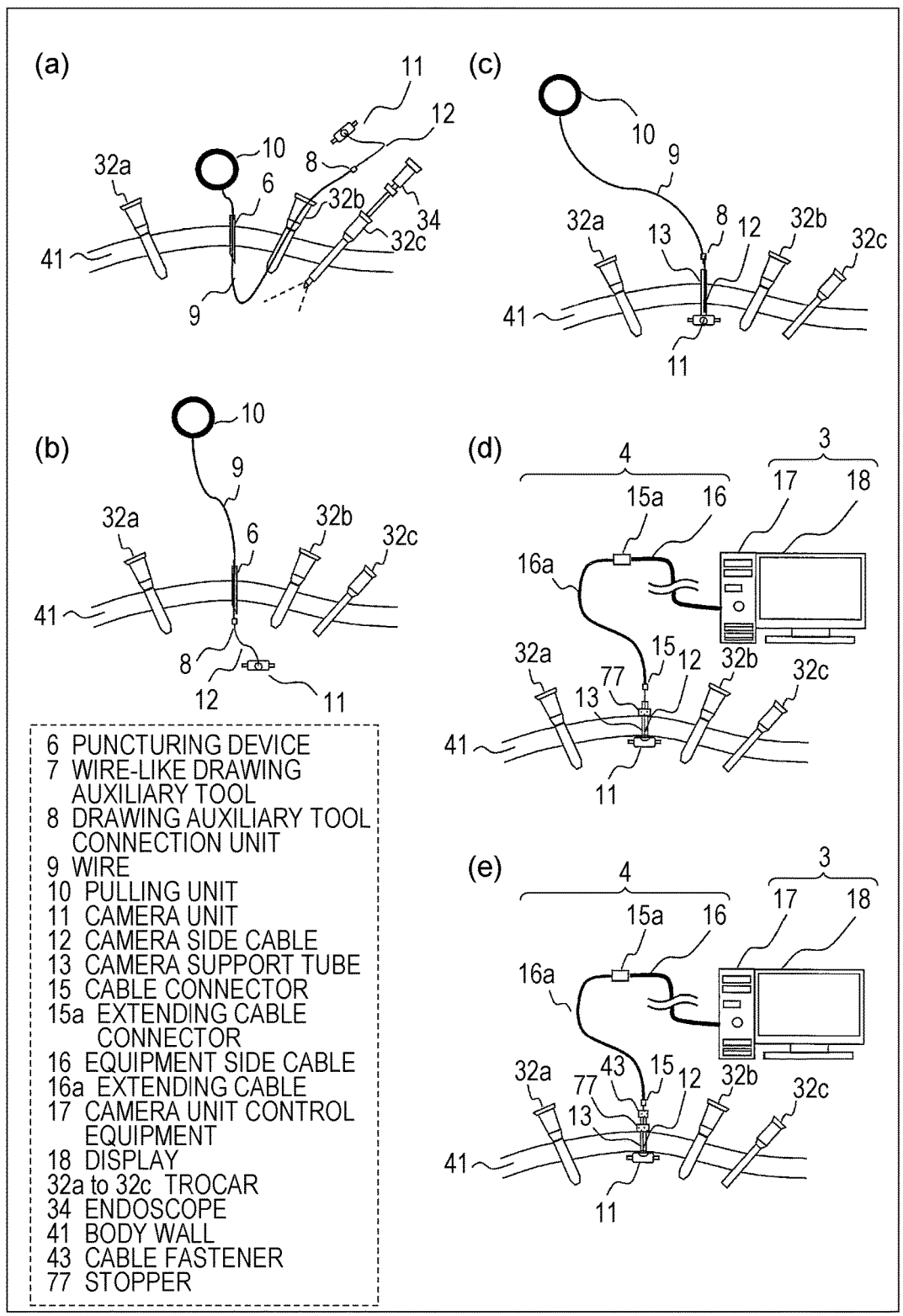
FIGS. 12(a) to 12(e) are schematic views illustrating the method for installing the imaging apparatus in the camera system for monitoring the inside of a body according to Embodiment 2, in a process order following FIGS. 11(a) to 11(d).
Figure 13:
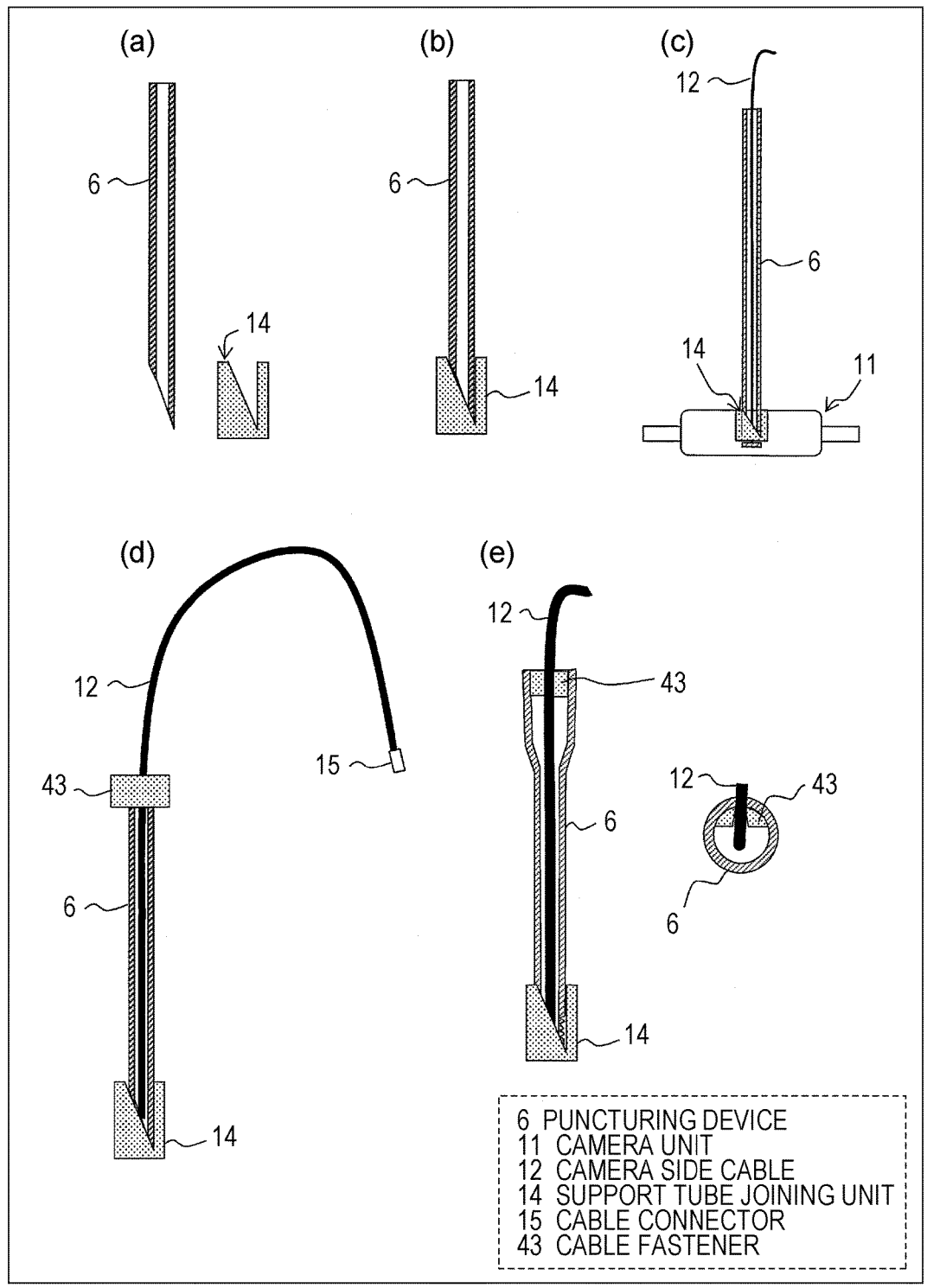
FIG. 13 is a view illustrating a modification example in which the puncturing device is used as the camera support tube according to Embodiment 2.
Figure 14:
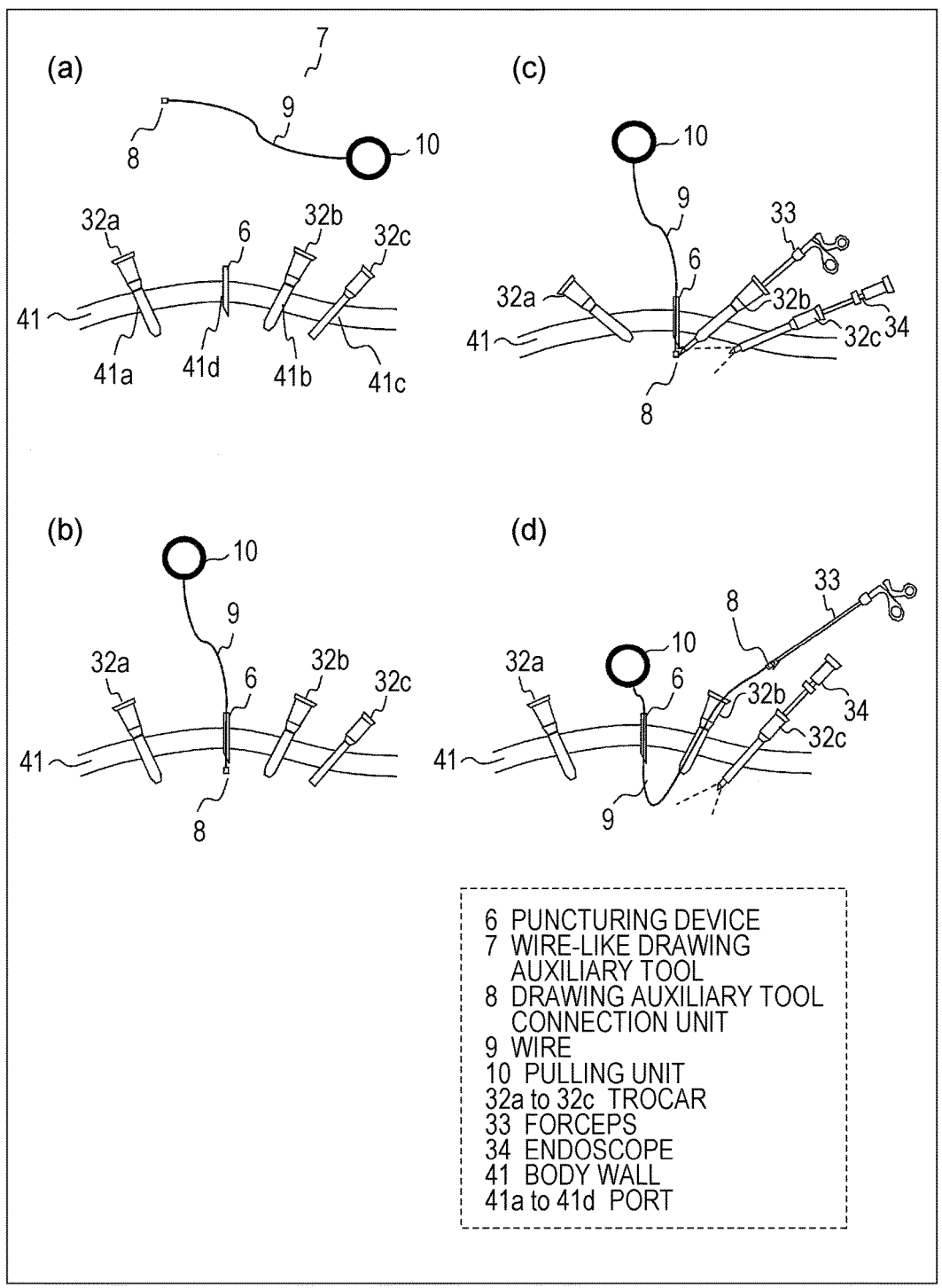
FIGS. 14(a) to 14(d) are schematic views illustrating a method for installing an imaging apparatus in a camera system for monitoring the inside of a body according to the modification example of Embodiment 2, in a process order.
Figure 15:
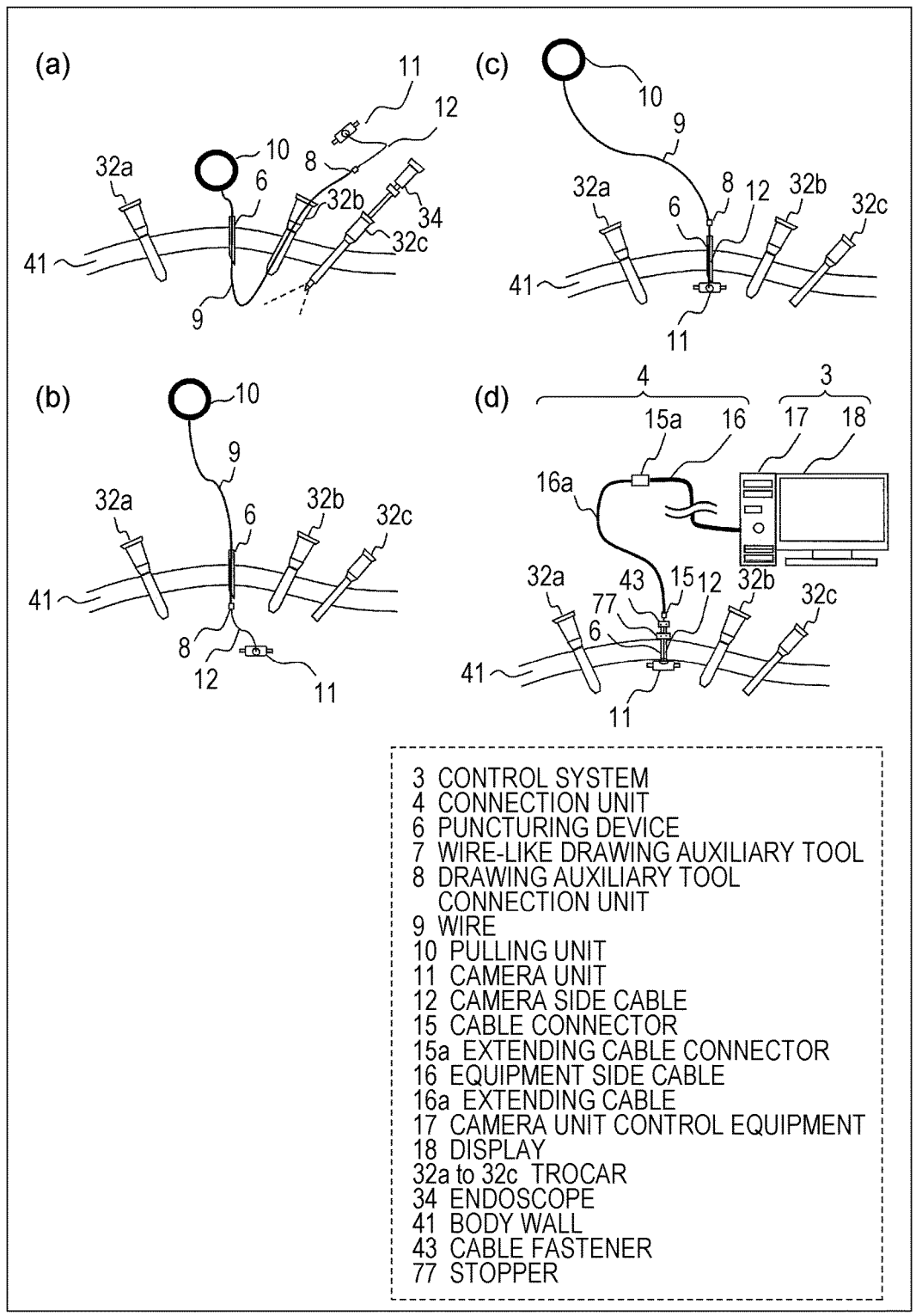
FIGS. 15(a) to 15(d) are schematic views illustrating the method for installing the imaging apparatus in the camera system for monitoring the inside of a body according to the modification example of Embodiment 2, in a process order following FIGS. 14(a) to 14(d).

FIGS. 11(*a*) to 11(*d*) and FIGS. 12(*a*) to 12(*e*) are schematic views illustrating a method for installing the imaging apparatus 2 in the camera system for monitoring the inside of a body 1 according to the embodiment, in a process order. Since the process in FIGS. 11(*a*) to 11(*d*) and the following process in FIGS. 12(*a*) and 12(*b*) are the same as those in Embodiment 1, the description thereof will be omitted.

As illustrated in FIG. 12(*c*), after further pulling the pulling unit 10 and extracting the puncturing device 6 from the body wall 41, the camera side cable 12 which is guided toward the outside of the body passes through the inside of the camera support tube 13, and inserts the camera support tube 13 into the body wall 41. The practitioner inserts the forceps 33 into the body cavity through the trocar 32, grips the support units 22 on both side surfaces of the camera unit 11 using two forceps 33 so that the support tube joining unit 14 of the camera unit 11 and the opening of the camera support tube 13 become parallel and close to each other, and joins the camera support tube 13 and the support tube joining unit 14 to each other by a method of screwing or inserting.

In a case of screwing, as illustrated in FIG. 12(*d*), the camera unit 11 is pulled up to the installation position of the body wall by using the camera support tube 13, and fixes the camera support tube 13 to the body wall 41 by using the stopper 77.

In a case of inserting, as illustrated in FIG. 12(*e*), after fixing the camera side cable 12 and the camera support tube 13 by the cable fastener 43, the camera unit 11 is pulled up to the installation position of the body wall by using the camera support tube 13, and the camera support tube 13 is fixed to the body wall 41 by using the stopper 77.

Since the puncturing device 6 is extracted and exchanged with the camera support tube 13, the outer diameter of the camera support tube 13 which is equivalent to that of the puncturing device 6 can be, for example, 3 mm. The diameter of the cable connector 15 becomes approximately 3 mm, but since the slit 223 is provided in the camera support tube 13, the camera side cable 12 having a diameter of approximately 2 mm can pass through the inside. Therefore, the wound of the installation unit of the camera unit 11 can be small, and minimal invasiveness can be achieved.

Next, as illustrated in FIGS. 12(*d*) and 12(*e*), the drawing auxiliary tool 7 is removed, the camera side cable 12 and the extending cable 16*a* are connected to each other by the cable connector 15, and the extending cable 16*a* and the equipment side cable 16 are connected to each other by the cable connector 15*a*. Furthermore, since the extending cable or the equipment side cable do not pass through the inside of the body, the cable having a large diameter can be used.

Accordingly, the entire image of the inside of the body captured by the camera unit 11 is displayed on the display 18 by the camera unit control equipment 17.

Figure 20:
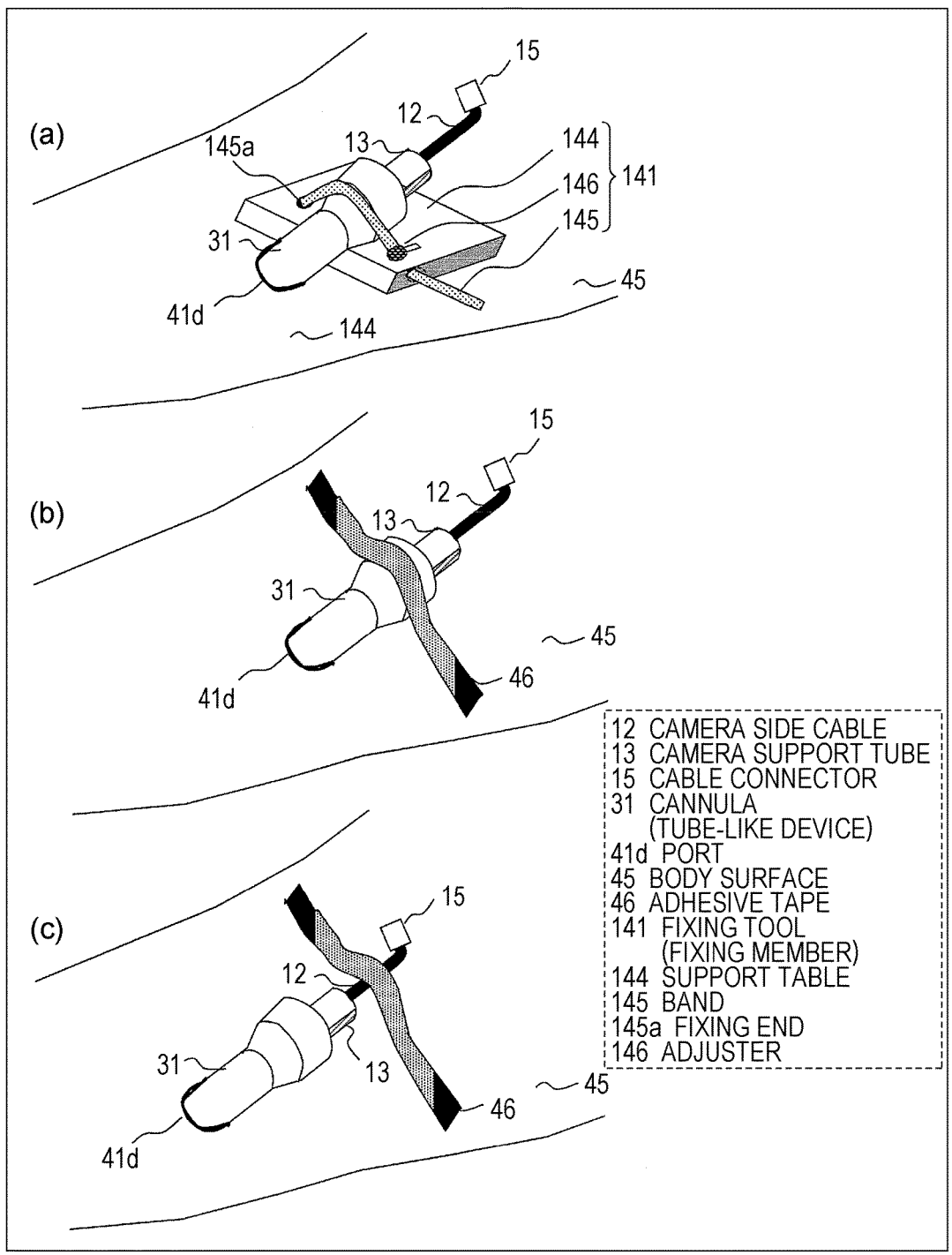
FIG. 20(a) is a perspective view illustrating an example of a schematic configuration of main parts of the camera system for monitoring the inside of a body according to Embodiment 3. In addition.
FIGS. 20(b) and 20(c) are respectively perspective views illustrating another example of the schematic configuration of the main parts of the camera system for monitoring the inside of a body according to Embodiment 3.

Next, while seeing the image of the display 18, the camera support tube 13 is operated, the camera unit 11 is moved, the height, the orientation, and the angle on the inside of the body cavity is adjusted, and fixing is performed by a fixing tool. An example of the fixing will be described later by using FIG. 20 combining with Embodiment 3.

After the positioning of the camera unit 11 is completed, the camera system for monitoring the inside of a body 1 is started to be used.

Accordingly, the practitioner can perform treatment using the forceps while enlarging and observing the work region (local region) on the display of the endoscope, and can also grasp the state (movement of the forceps or the like, a bleeding site, and a residual, such as gauze, outside the work region) outside the work region on the display 18.

Furthermore, in the installation method illustrated in FIGS. 11(*a*) to 11(*d*) and FIGS. 12(*a*) to 12(*e*), a method for guiding the drawing auxiliary tool 7 through the puncturing device 6 is described, but the invention is not limited thereto. After performing the puncturing in the process of FIG.

11(a), the puncturing device 6 may be exchanged with the camera support tube 13, and the drawing auxiliary tool 7 may be guided through the camera support tube 13.

<Method for Collecting Camera Unit 11>

An order of collecting the camera unit 11 after the surgery is finished, will be described.

First, the cable connector 15 and the cable fastener 43 are removed, and the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out the cut organ.

<Effect>

As described above, according to the embodiment, during the endoscopic surgery, it is possible to install an apparatus which can grasp the situation on the inside of the body in a wide viewing field and can substantially enhance safety, during a short period of time without stressing out a practitioner by a simple and safe method only by generating a minimal wound which is equivalent to the size of the outer diameter of the camera side cable 12.

Modification Example 1

(Method for Joining Camera Support Tube 13 and Camera Unit 11)

In the embodiment, a case where the camera support tube 13 and the camera unit 11 are screwed to each other as the locking male screw 123 is provided in the camera support tube 13 and the locking female screw 23 is provided in the support tube joining unit 14, will be described as an example.

However, the method for joining the camera support tube 13 and the camera unit 11 to each other is not limited thereto, and any shape in which the camera support tube 13 and the support tube joining unit 14 are able to be fitted to each other may be employed.

FIGS. 10(d) to 10(h) are respectively sectional views illustrating modification examples of the camera support tube 13 and the support tube joining unit 14 according to the embodiment.

FIG. 10(d) illustrates an example in which a locking hole 323 is provided in the camera support tube 13 and a locking claw 423 is provided in the support tube joining unit 14.

FIG. 10(e) illustrates an example in which a locking claw 523 is provided in the camera support tube 13 and a locking hole 623 is provided in the support tube joining unit 14.

In addition, FIGS. 10(d) and 10(e) are sectional views illustrating each section of the camera support tube 13 and the support tube joining unit 14 in each modification example.

As illustrated in FIGS. 10(d) and 10(e), in the camera support tube 13 according to the modification example, a part further at a tip part than the locking hole 323 has a tapered shape. Therefore, the tip end (inside of the body) of the camera support tube 13 is not hooked to the locking claw 423 of the support tube joining unit 14, and when pushing the camera support tube 13 until the tip end thereof reaches a deep part of the support tube joining unit 14, the locking hole 323 is fitted to the locking claw 423.

However, the camera support tube 13 is not limited to the above-described structure. The thicknesses of both end parts of the camera support tube 13 may be the same.

In the modification examples, in order to separate the camera unit 11 and the camera support tube 13 from each other, it is preferable to design that the engagement of the locking claw 423 and the locking hole 323 or the engagement of the locking claw 523 and the locking hole 623 are released by applying a force which is equal to or greater than a threshold value, for example, by giving elasticity to the locking claws 423 and 523, or by giving flexibility to the support tube joining unit 14. Otherwise, it is desirable to design that the locking claw 423 retreats (changes to a state of not being protruded) from the wall surface in the opening of the support tube joining unit 14, or the locking claw 523 retreats from the surface of the camera support tube 13, by an external force, such as a magnetic force or electricity.

Instead of joining the camera support tube 13 and the support tube joining unit 14 to each other by using the locking male screw 123 and the locking female screw 23, or by using the locking claws 423 and 523 and the locking holes 323 and 623 as described above, it is also possible to join the camera support tube 13 and the support tube joining unit 14 to each other by forming the inner wall of the support tube joining unit 14 with the elastic material, such as rubber, and by pressing the camera support tube 13 to the support tube joining unit 14.

In FIG. 10(f), a case where a tip part of the camera support tube 13 has a tapered shape, is also illustrated as an example. This case is another modification example in which a method for pulling and fixing the camera side cable 12 not using the locking hole and the locking claw.

Another modification example in which the cable fastener 43 is provided in the camera support tube 13 is illustrated in FIGS. 10(g) and 10(h).

FIG. 10(g) is a view in which a sectional view and an upper view of the camera support tube 13 are aligned when the cable fastener 43 (locking member) is provided at the end part 13b on the outside of the body in the camera support tube 13. FIG. 10(h) is a view in which a sectional view and an upper view of the camera support tube 13 are aligned when the camera side cable 12 passes through the camera support tube 13.

As described in Embodiment 1, the camera side cable 12 is connected to the equipment side cable 16 via the cable connector 15. In the modification example, in order to lock the camera side cable 12 to the camera support tube 13, as illustrated in FIGS. 10(g) and 10(h), the cable fastener 43 (locking member) is provided at the end part 13b on the outside of the body of the camera support tube 13.

According to the embodiment, by fixing the camera side cable 12 to the camera support tube 13 using the cable fastener 43, it is possible to temporarily stop the camera side cable 12 in the middle of the installation work of the camera unit 11, and there is also an advantage that the workability is improved. In addition, even when the camera side cable 12 is pulled on the outside of the body after the installation, there is also an advantage that a load is not applied to the connection unit of the camera unit and the camera side cable 12, and it is possible to prevent the camera side cable from being cut.

<Schematic Configuration of Camera Support Tube 13>

Here, first, a schematic configuration of the camera support tube 13 according to the modification example will be described.

As illustrated in FIG. 10(g), the camera support tube 13 which is used in the modification example includes a head unit 113 and a leg unit 114, and has a configuration which is similar to that of the camera support tube 13 according to Embodiment 2, except that the camera support tube 13 is a funnel-shaped tube in which the inner diameter of the head unit 113 is greater than the inner diameter of the leg unit 114.

The end part 13a on the leg unit 114 side of the camera support tube 13 according to the modification example is guided toward the inside of the body through the body wall 41, such as an abdominal wall.

In addition, in the modification example, the leg unit 114 of the camera support tube 13 has a cylindrical shape. Therefore, it is easy to combine the camera support tube 13 with a general cannula which is the same cylindrical tube that will be described later in Embodiment 3.

<Schematic Configuration of Cable Fastener 43>

As described above, in the camera support tube 13 used in the modification example, the end part 13b (outside of the body) on the head unit 113 side has a shape which is thicker than that of the end part 13a on the leg unit 114 side (inside of the body) inserted into the body.

The cable fastener 43 is provided at the end part 13b on the head unit 113 side in the camera support tube 13.

As illustrated in FIGS. 10(g) and 10(h), the cable fastener 43 has a longitudinal groove 43a which extends in the axial direction of the camera support tube 13, and of which the width narrows (a lateral section is tapered in the outward orientation) to the outside (a direction of a side surface) from the center of the camera support tube 13. In addition, as the longitudinal groove 43a, instead of providing the tapered longitudinal groove in the cable fastener 43, the cable fastener 43 is configured of the elastic member, and by providing a cut-out as the longitudinal groove 43a in the cable fastener 43, the camera side cable 12 may also be held using the biasing force by the elastic material.

According to the modification example, in this manner, by fixing the camera side cable 12 to a bottom part (a part having a narrowed width) of the longitudinal groove 43a of the cable fastener 43, it is possible to fix the camera side cable 12 to the camera support tube 13.

Therefore, according to the modification example, it is possible to fix the camera side cable 12 and the camera support tube 13 using the cable fastener 43 as illustrated in FIG. 10(h).

In addition, the cable fastener 43 may be integrally formed with the camera support tube 13, and may be separately formed. In other words, the camera side cable 12 may be fixed by inserting the cable fastener 43 into the camera support tube 13 as a separated component after the camera side cable 12 passes through the camera support tube 13.

Modification Example 2

Method of Use of Puncturing Device 6 as Camera Support Tube 13

In the embodiment, a case where the camera support tube 13 is inserted and the camera unit 11 is fixed after extracting the puncturing device 6, is described as an example.

However, the camera support tube 13 is not limited thereto, and may have a shape in which the puncturing device 6 and the support tube joining unit 14 are fitted to each other, and the puncturing device 6 may be used as the camera support tube 13.

The method thereof will be described by using FIGS. 13(a) to 13(e).

The camera unit 11 illustrated in FIG. 13(c) includes the recessed support tube joining unit 14 (joining unit) on the upper surface thereof. The support tube joining unit 14 has an annular opening shape (hole structure) when viewed from above as illustrated in FIG. 9(b).

FIG. 13(a) is a sectional view illustrating each sections of the puncturing device 6 and the support tube joining unit 14 according to the modification example 2, and FIG. 13(b) is a sectional view illustrating a joined state of the puncturing device 6 and the support tube joining unit 14. In addition, in FIG. 13(b), the camera side cable 12 is omitted. The support tube joining unit 14 has a recessed shape which corresponds to the shape of the needle-like puncturing device 6.

FIG. 13(c) is a view in which the camera unit 11 and the camera side cable 12 are added in FIG. 13(b), and by rotating the puncturing device 6 in the axial direction while pulling the camera side cable 12, it is possible to be fitted to the support tube joining unit 14.

Next, by making the cable fastener 43 pass through the camera side cable 12 while pulling the camera side cable 12, and by pushing the camera side cable 12 to the end part of the puncturing device 6, the camera side cable 12 is fixed. Since the tip end of the puncturing device 6 has an asymmetric shape which is diagonally cut, when the puncturing device 6 is rotated, it is possible to rotate the camera unit 11.

In addition, a structure in which the cable fastener 43 is provided in the puncturing device 6 as illustrated in FIG. 13(e) may be employed.

<Method for Installing Camera System for Monitoring Inside of Body 1>

Next, both the method for installing the imaging apparatus 2 in the camera system for monitoring the inside of a body 1 according to the modification example 2, and the method of use, will be described.

FIGS. 14(a) to 14(d) and FIGS. 15(a) to 15(d) are schematic views illustrating the method for installing the imaging apparatus 2 in the camera system for monitoring the inside of a body 1 according to the modification example, in a process order. Since the process in FIGS. 14(a) to 14(d) and the following process in FIGS. 15(a) and 15(b) are the same as those in Embodiment 2, the description thereof will be omitted.

As illustrated in FIG. 15(c), the pulling unit 10 is further pulled, and the camera side cable 12 is guided toward the outside of the body through the puncturing device 6. By rotating the puncturing device 6 while pulling the camera side cable 12, it is possible to simply make the puncturing device 6 fit into the support tube joining unit 14.

Next, as illustrated in FIG. 15(d), after fixing the camera side cable 12 and the puncturing device 6 to each other by the cable fastener 43, the camera unit 11 is pulled up to the installation position of the body wall by using the puncturing device 6, and the camera support tube 13 is fixed to the body wall 41 by using the stopper 77.

Since the puncturing device 6 is used as the camera support tube as it is, the installation method becomes simplified, and the installation time is reduced. In addition, when the outer diameter of the puncturing device 6 can be approximately 3 mm when the diameter of the cable connector 15 is approximately 2 mm. Therefore, the wound of the installation unit of the camera unit 11 can be small, and minimal invasiveness can be achieved.

Next, as illustrated in FIG. 15(d), the drawing auxiliary tool 7 is removed, the camera side cable 12 and the extending cable 16a are connected to each other by the cable connector 15, and the extending cable 16a and the equipment side cable 16 are connected to each other by the cable connector 15a. Furthermore, since the extending cable or the equipment side cable do not pass through the inside of the body, the cable having a large diameter can be used.

Accordingly, the entire image of the inside of the body captured by the camera unit 11 is displayed on the display 18 by the camera unit control equipment 17.

Next, while seeing the image of the display 18, the puncturing device 6 is operated, the camera unit 11 is moved, the height, the orientation, and the angle on the inside of the body cavity is adjusted, and fixing is performed by the fixing tool. An example of the fixing will be described later by using FIG. 15 combining with Embodiment 3.

After the positioning of the camera unit 11 is completed, the camera system for monitoring the inside of a body 1 is started to be used.

Accordingly, the practitioner can perform treatment using the forceps while enlarging and observing the work region (local region) on the display of the endoscope, and can also grasp the state (movement of the forceps or the like, a bleeding site, and a residual, such as gauze, outside the work region) outside the work region on the display 18.

<Method for Collecting Camera Unit 11>

An order of collecting the camera unit 11 after the surgery is finished, will be described.

First, the stopper 77, the cable connector 15, and the cable fastener 43 are removed, and the puncturing device 6 is extracted to the outside of the body.

Next, the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out the cut organ.

<Effect>

As described above, according to the embodiment, during the endoscopic surgery, it is possible to install an apparatus which can grasp the situation on the inside of the body in a wide viewing field and can substantially enhance safety, during a short period of time without stressing out a practitioner by a simple and safe method only by generating a minimal wound which is equivalent to the size of the outer diameter of the puncturing device 6.

Embodiment 3

Still another embodiment of the present invention will be described based on FIGS. 16 to 20 as follows. In addition, in the embodiment, mainly, differences from Embodiments 1 and 2 will be described, configuration elements which have the same functions as those of the configuration elements used in Embodiments 1 and 2 will be given the same reference numerals, and the description thereof will be omitted. In addition, in the embodiment, it is also needless to say modifications similar to those of Embodiments 1 and 2 are possible.

<Schematic Configuration of Camera System for Monitoring Inside of Body>

FIG. 16 is a schematic view illustrating a schematic configuration of the camera system for monitoring the inside of a body 1 according to the embodiment.

As illustrated in FIG. 16, the camera system for monitoring the inside of a body 1 according to the embodiment is provided with the imaging apparatus 2, the camera support tube 13 (support tube), the control system 3, the connection unit 4, a cannula 31 (bushing, holding tube) which serves as a support tube fixing member (support tube fixing means, fixing member), and the drawing auxiliary tool 5. As the camera support tube 13, the needle-like puncturing device used in puncturing may be used as it is.

Hereinafter, each configuration element will be described in detail. Description of the control system 3, the connection unit 4, and the drawing auxiliary tool 5 will be omitted since the control system 3, the connection unit 4, and the drawing auxiliary tool 5 are the same as those of Embodiment 1. In addition, description of the imaging apparatus 2 will be omitted since the imaging apparatus 2 is the same as that of Embodiment 2.

<Schematic Configuration of Camera Support Tube 13>

As illustrated in FIG. 16, the camera support tube 13 is a support tube which supports the camera unit 11 as being joined to the camera unit 11 on the inside of the body in a state where the camera side cable 12 passes through the inside thereof, and is drawn out toward the outside of the body.

From the viewpoint of the joining strength with the camera unit 11, the camera support tube 13 is formed of a hard material. The material of the camera support tube 13 is not particularly limited if the material has rigidity which makes it possible to obtain the joining strength that can stably support the camera unit 11, and which makes it possible to fix the camera unit 11 at a desirable position and orientation. For example, stainless steel, ceramics (fine ceramics), or reinforced plastic may be used.

Figure 17:
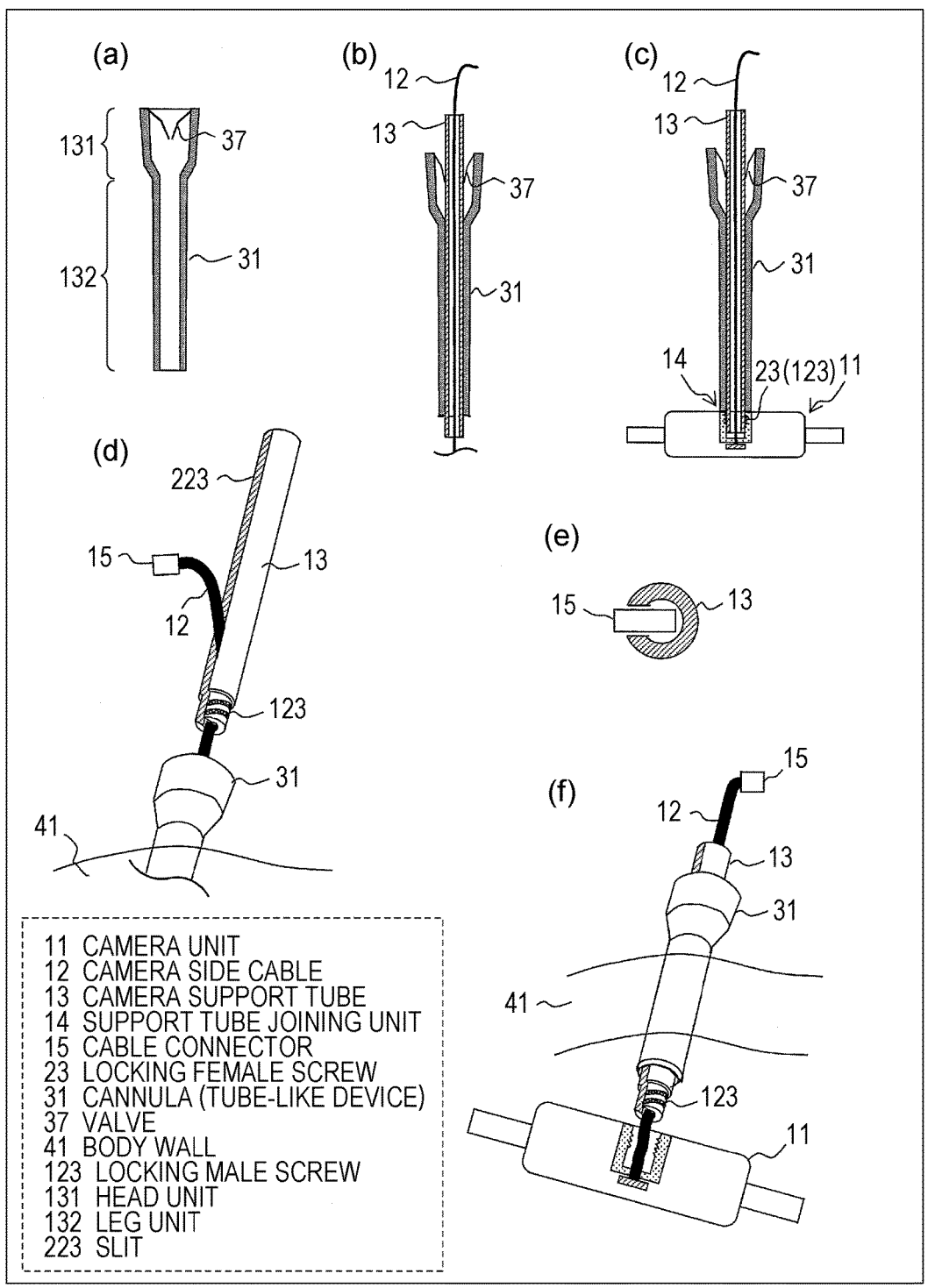
FIG. 17(a) is a sectional view illustrating a schematic configuration of a cannula according to Embodiment 3.
FIG. 17(b) is a sectional view illustrating a state where the camera support tube illustrated in FIGS. 10(a) to 10(f) is inserted into the cannula illustrated in FIG. 17(a)
FIG. 17(c) is a sectional view illustrating an example of a joined state of the camera support tube inserted into the cannula and the camera unit illustrated in FIG. 9.
FIGS. 17(d) and 17(f) are perspective views illustrating a detailed process illustrated in FIG. 19(c)
FIG. 17(e) is a plan view illustrating a relationship between the size of a cable connector illustrated in FIG. 17(d) and the size of the camera support tube.
Figure 18:
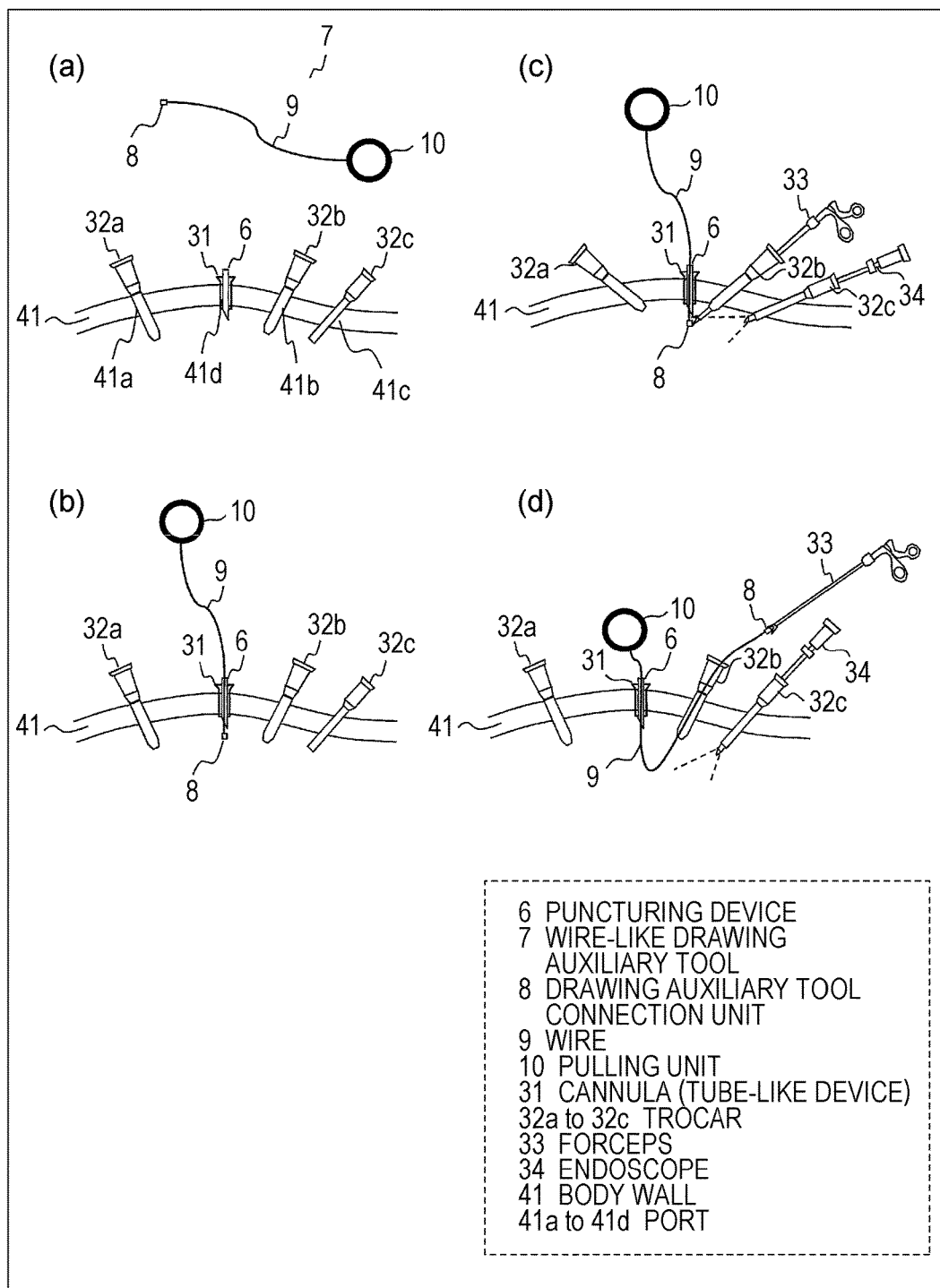
FIGS. 18(a) to 18(d) are schematic views illustrating a method for installing the imaging apparatus in the camera system for monitoring the inside of a body according to Embodiment 3, in a process order.
Figure 19:
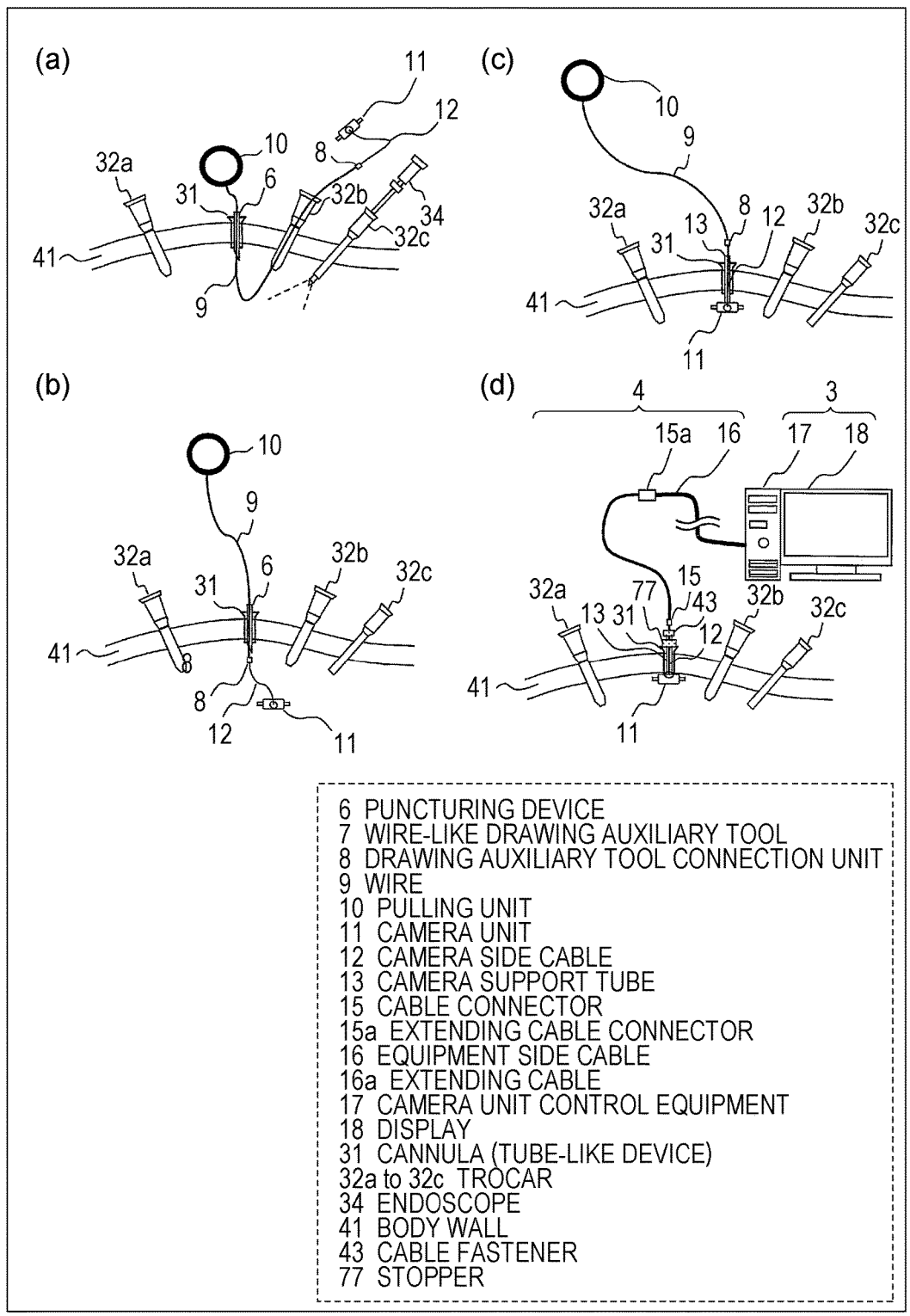
FIGS. 19(a) to 19(d) are schematic views illustrating the method for installing the imaging apparatus in the camera system for monitoring the inside of a body according to Embodiment 3, in a process order following FIGS. 18(a) to 18(d).

One end part 13a (first end part) of the camera support tube 13 is guided toward the inside of the body through the body wall 41, such as an abdominal wall. At this time, one end part 13a of the camera support tube 13 may be directly guided toward the inside of the body, or as illustrated in FIG. 17, one end part 13a may be guided toward the inside of the body penetrating the camera support tube 13 on the inside of the cannula 31, by using the cannula 31 inserted into the body wall 41. In addition, as illustrated in the modification example 2, the needle-like puncturing device 6 which is used in puncturing may be used as it is as the camera support tube 13.

In a case where the cannula 31 is used, as the camera support tube 13, the camera support tube 13 which is longer than the cannula 31 in the axial direction is used so that the one end part 13a and the other end part 13b (second end part) are exposed from the cannula 31 in a state where the camera support tube 13 is inserted into the cannula 31. In addition, the camera support tube 13 having a size (thickness) to have a void between an outer wall of the camera support tube 13 and an inner wall of the cannula 31 is used in a state of penetrating the camera support tube 13 in the cannula 31 in order to make it possible to rotate the camera support tube 13 around the axis in the cannula 31.

The end part 13a guided toward the inside of the body joins with the camera unit 11 by the support tube joining unit 14.

<Support Tube Fixing Member>

The camera system for monitoring the inside of a body 1 according to the embodiment is provided with the cannula 31 (holding tube) and a fixing member, as a support tube fixing member (support tube fixing means) which fixes the camera support tube 13 on the outside of the body.

(Cannula 31)

Figure 7:
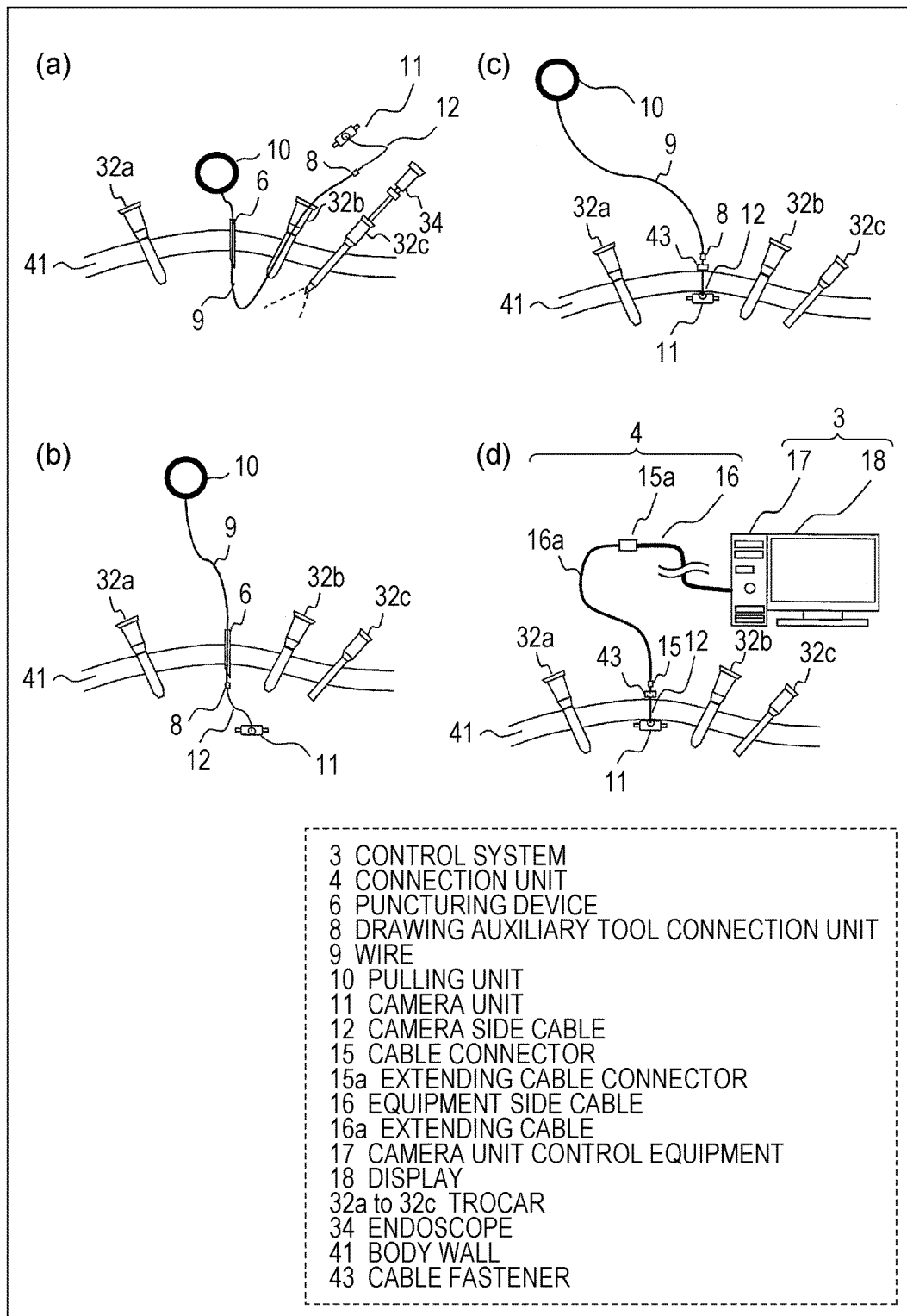
FIGS. 7(a) to 7(d) are schematic views illustrating the method for installing the imaging apparatus in the camera system for monitoring the inside of a body according to Embodiment 1, by a process order following FIGS. 6(a) to 6(d).

FIG. 17(a) is a sectional view illustrating a schematic configuration of the cannula 31 used in the embodiment, FIG. 17(b) is a sectional view illustrating a state where the camera support tube 13 illustrated in FIGS. 10(a) to 10(h) is inserted into the cannula 31 illustrated in FIG. 17(a), and FIG. 17(c) is a sectional view illustrating an example of a joined state of the camera support tube 13 inserted into the cannula 31 and the camera unit 11 illustrated in FIG. 7.

As illustrated in FIG. 17(a), the cannula 31 which is used in the embodiment is a funnel-like tube (tube-like device) which includes a head unit 131 and a leg unit 132, and in which the inner diameter of the head unit 131 is greater than the inner diameter of the leg unit 132.

Therefore, in the cannula 31, an end part 31b (outside of the body) on the head unit 131 side is greater than an end part 31a on the leg unit 132 side (inside of the body) which is inserted into the body, and when the cannula 31 is inserted into the body wall 41, the head unit 131 functions as a stopper.

Accordingly, there is not case where the camera support tube 13 falls out on the inside of the body, and the cannula 31 can be fixed to the body wall 41.

In addition, the cannula 31 includes a valve 37, and the valve 37 has a valve structure which pressingly expands when an external force is applied toward the thin end part 31a (inside of the body) from the thick end part 31b (outside of the body) at the center part thereof.

Therefore, as illustrated in FIG. 17(b), when the camera support tube 13 is inserted into the cannula 31 through the valve 37, the valve 37 pressingly expands by the camera support tube 13, and the camera support tube 13 is tightly fastened by a biasing force caused by the restoration properties. As a result, the camera support tube 13 is fixed to the cannula 31.

In addition, it is preferable that the diameter of the cannula 31 is small in order to realize minimal invasiveness. Specifically, it is preferable that the diameter of the cannula 31 is equal to or less than 3 mm.

(Fixing Camera Support Tube 13 to Cannula 31 and Joining Camera Support Tube 13 to Camera Unit 11)

Here, a manner of inserting the camera support tube 13 into the cannula 31 and joining the camera support tube 13 to the camera unit 11, will be described with reference to FIGS. 17(b) and 17(c).

In a case where the camera unit 11 joins with the camera support tube 13 on the inside of the body, first, as illustrated in FIG. 17(b), in a state of passing through the camera side cable 12 inside the camera support tube 13, one end part 13a of the camera support tube 13 is pushed against the thick end part 31b (outside of the body) of the cannula 31, and until the end part 13a of the camera support tube 13 is exposed from the cannula 31, the camera support tube 13 is inserted into the cannula 31. At this time, as the valve 37 is pressingly expanded by the camera support tube 13, and the camera support tube 13 is biased due to the restoration properties, the camera support tube 13 is fixed to the cannula 31. In addition, the other end part 13b (outside of the body) of the camera support tube 13 is also exposed from the cannula 31.

Next, as illustrated in FIG. 17(c), by inserting and screwing the locking male screw 123 of the end part 13a on the inside of the body of the camera support tube 13 into the locking female screw 23 of the support tube joining unit 14, the locking male screw 123 is fitted to the locking female screw 23, and the camera unit 11 and the camera support tube 13 are joined to each other at a high mechanical strength.

In addition, FIG. 17(c) illustrates a state where the camera support tube 13 is pulled up and the camera unit 11 comes into contact with the end part 31a of the cannula 31 on the inside of the body after joining the camera support tube 13 and the camera unit 11 to each other by the support tube joining unit 14.

The camera support tube 13 is fixed to the cannula 31 which can move in the direction of the external force by applying the external force to the camera support tube 13, for example, by applying the force to the camera support tube 13 by one hand in a state where the practitioner pushes the cannula 31 by the other hand.

In other words, by applying the external force to the camera support tube 13 in the vertical direction (axial direction) or in the rotational direction (circumferential direction), the cannula 31 can move the camera support tube 13 in the vertical direction or in the rotational direction, and when the external force is not applied, the camera support tube 13 can be maintained (fixed) at an arbitrary position in the height direction and in the rotational direction of the camera support tube 13.

(Fixing Member)

A fixing tool (second fixing member) which fixes the camera support tube 13 in a state of being maintained at a constant angle with respect to a body surface 45, by fixing the camera support tube 13 to a fixture (fixed body) fixed to the outside of the body, will be described.

FIGS. 20(a) to 20(c) are perspective views illustrating an example of a schematic configuration of main parts of the camera system for monitoring the inside of a body 1 according to the embodiment. FIGS. 20(a) to 20(c) are respectively perspective views illustrating an example of the support tube fixing member.

Example 1 of Support Tube Fixing Member

As illustrated in FIG. 20(a), the camera system for monitoring the inside of a body 1 according to the example includes the cannula 31 illustrated in FIGS. 17(a) to 17(c), and a fixing device 141 (dedicated device), as the support tube fixing member.

In the example, as the fixing tool, by using the dedicated fixing device 141 which can directly fix the camera support tube 13 to the body surface 45, the camera support tube 13 which is fixed to the cannula 31 is fixed.

The fixing device 141 according to the example includes a support table 144 provided with an adhesive layer, which is not illustrated, on one surface (contact surface which is in contact with the body surface 45); an accessory band 145 (belt-like string) which is fixed to a surface opposite to the adhesive layer in the support table 144; and an adjuster 146 which adjusts the fixing length of the band 145.

In the band 145, while one end part is directly fixed to the support table 144, the other end part is fixed to the support table 144 via the adjuster 146. The fixing length of the band 145 can be arbitrarily adjusted by adjusting the length from a fixing end 145a of the band 145 which is directly fixed to the support table 144, to the adjuster 146 which fixes the other end part of the band 145 that is a free end to the support table 144.

In the example, by fixing the cannula 31 which fixes the camera support tube 13, to the support table 144 by the band 145, in a state where the fixing device 141 is fixed to the body surface 45 by the adhesive layer, the camera support tube 13 is fixed to the body surface 45 via the cannula 31.

Therefore, in the example, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, by adjusting the fixing position of the cannula 31 by the band 145, it is possible to change the fixing angle (inclination) of the cannula 31 and the camera support tube 13 with respect to the body surface 45. Accordingly, it is also possible to fix the cannula 31 and the camera support tube 13 at a desirable angle, and to arbitrarily change the direction of the visual field of the camera unit 11.

Accordingly, it is possible for the camera support tube 13 to be fixed in a desirable state.

In the example, the adjuster 146 is used in adjusting the fixing length of the band 145 as illustrated in FIG. 20(a), but a method for adjusting the fixing length of the band 145 is not limited thereto. For example, instead of using the adjuster 146, as the band 145, a band provided with a surface fastener, such as a magic tape (registered trademark), may be used.

In the example illustrated in FIG. 20(a), a case where the cannula 31 is tied to the support table 144 by fastening (pressing) the cannula 31 with the band 145, is described, but the camera support tube 13 may be tied to the support table 144 by fastening (pressing) the camera support tube 13 by the band 145.

In a case where the camera support tube 13 is fastened by the band 145, the camera support tube 13 may be fixed at a desirable position by fastening the camera support tube 13 with the band 145 again after adjusting the fixing length of the band 145, loosening the band 145, moving the camera support tube 13 or the support table 144, and adjusting the position of the camera support tube 13. Otherwise, by adjusting the fixing length of the band 145, giving elasticity to the band 145, and adjusting fastening strength, the camera support tube 13 may be fixed so that the camera support tube 13 can be moved as a force which is equal to or greater than a certain level is applied to the camera support tube 13.

In the example, as described above, a case where the cannula 31 illustrated in FIGS. 17(a) to 17(c) is used as the cannula 31, is described as an example. However, in a case where the camera support tube 13 is fastened by the band 145, since the movement of the camera support tube 13 is further restricted by the band 145, the camera support tube 13 is not necessarily fixed to the cannula, and a general cannula can be used as the cannula.

The shape or the material of the dedicated fixing device which is used in the above-described example are not particularly limited if the fixing device can be fixed to the body surface.

In addition, in the above-described example, a case where each fixing device is fixed to the body surface is described as an example, but the embodiment is not limited thereto.

For example, the camera support tube 13 or the cannula 31 may be fixed by the dedicated fixing device installed on an operating table.

For example, as an arm, a so-called joint arm or an articulated arm which has at least one joint unit, can bend the arm by the joint unit, and can freely change a bending angle, is used, the arm may be fixed to the operating table or to the fixing device installed on the operating table or in the operating room, instead of being fixed to the support table or the body surface 45, and the support table provided with the arm may be fixed to the fixing device installed on the operating table or in the operating room. Accordingly, since it is possible to make the reach from the fixing position of the fixing device to a clamp unit long, effects similar to those in a case where the fixing device is fixed to the body surface 45, which is close to the affected part, can be achieved.

Example 2 of Support Tube Fixing Member

Another example of the support tube fixing member of the present invention will be described.

FIG. 20(b) is a perspective view illustrating an example of a schematic configuration of main parts of the camera system for monitoring the inside of a body 1 according to the embodiment.

The camera system for monitoring the inside of a body 1 according to the embodiment is provided with the cannula 31 illustrated in FIGS. 17(a) to 17(c) and an adhesive tape 46, as the support tube fixing member.

In the embodiment, by using the adhesive tape 46 which can be directly fixed to the body surface 45, the camera support tube 13 fixed to the cannula 31 is fixed. In addition, in the embodiment, the camera support tube 13 is indirectly fixed to the body surface 45 via the cannula 31.

As the adhesive tape 46, an adhesive tape which has an adhesive layer in a contact unit which is in contact with the body surface, and which is generally used in surgery, can be used. The adhesive tape 46 is provided with the adhesive layer which is not illustrated, on one surface (contact surface which is in contact with the body surface 45), and can be directly fixed to the body surface 45 by adhesive properties of the adhesive layer.

In addition, in the embodiment, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, in the embodiment, by changing the fixing position (that is, the position to which a pressing force caused by the adhesive tape 46 is applied to the cannula 31) of the adhesive tape 46 in the cannula 31, it is possible to change a fixing angle (inclination) of the cannula 31 and the camera support tube 13 with respect to the body surface 45. Accordingly, in the embodiment, it is also possible to fix the cannula 31 and the camera support tube 13 at a desirable angle, and to arbitrary change the viewing field direction of the camera unit 11.

In addition, for example, under the cannula 31 (that is, between the cannula 31 and the body surface 45), by nipping an object having a desirable thickness similar to the support table 144 illustrated in FIG. 20(a), as a fixing height adjusting member which adjusts the fixing height of the cannula 31, the fixing angle (inclination) of the cannula 31 and the camera support tube 13 may be changed. In other words, the camera system for monitoring the inside of a body 1 according to the embodiment may further be provided with the fixing height adjusting member which is not illustrated in addition to the cannula 31 and the adhesive tape 46, as the support tube fixing member.

Accordingly, in the embodiment, it is also possible for the camera support tube 13 to be fixed in a desirable state.

In addition, in the example illustrated in FIG. 20(b), a case where the cannula 31 is fixed by the adhesive tape 46 by adhering the adhesive tape 46 to the cannula 31, is illustrated as an example, but in the embodiment, the camera support tube 13 may also be directly fixed by the adhesive tape 46 by adhering the adhesive tape 46 to the camera support tube 13.

In a case where the camera support tube 13 is directly fixed by the adhesive tape 46, in a case where the practitioner changes the position of the camera support tube 13 after operating the camera support tube 13, adjusting the position of the camera support tube 13, and fixing the camera support tube 13 using the adhesive tape 46, the practitioner operates the camera support tube 13 and adjusts the position of the camera support tube 13 again by peeling the adhesive tape 46. After this, again, the camera support tube 13 may be fixed by the adhesive tape 46.

Accordingly, even in a case where the camera support tube 13 is directly fixed by the adhesive tape 46, it is possible for the camera support tube 13 to be fixed in a desirable state.

In addition, in the embodiment, in a case where the camera support tube 13 is directly fixed by the adhesive tape 46, since the movement of the camera support tube 13 is further restricted by the adhesive tape 46, the camera support tube 13 is not necessarily fixed to the cannula, and a general cannula can be used as the cannula.

Example 3 of Support Tube Fixing Member

Still another example of the present invention will be described based on FIGS. 10(g), 10(h), and 20(c) as follows. In addition, in the embodiment, mainly, differences from other embodiments will be described, configuration elements which have the same functions as those of the configuration elements used in other embodiments will be given the same reference numerals, and the description thereof will be omitted. In addition, in the embodiment, it is also needless to say modifications similar to those of other embodiments are possible.

In the above-described other embodiments, a case where the camera support tube 13 or the cannula 31 which fixes the camera support tube 13, are fixed to the outside of the body by the fixing tool, is described as an example.

In the embodiment, a case where the camera support tube 13 is fixed by fixing the camera side cable 12 to the camera support tube 13, and by fixing the camera side cable 12 to the outside of the body by the fixing tool, is described as an example.

FIG. 10(g) is a view in which the sectional view and the upper view of the camera support tube 13 when the cable fastener 43 (locking member) is provided at the end part 13b on the outside of the body in the camera support tube 13, are aligned, FIG. 10(h) is a view in which the sectional view and the upper view of the camera support tube 13 when the camera side cable 12 passes through the camera support tube 13, are aligned, and FIG. 20(c) is a perspective view illustrating an example of the schematic configuration of the main parts of the camera system for monitoring the inside of a body 1 according to the embodiment.

The camera system for monitoring the inside of a body 1 according to the embodiment is provided with, for example, the cannula 31, the cable fastener 43, and the adhesive tape 46 which are illustrated in FIGS. 10(g), 10(h), and 20(c), and the camera side cable 12 also functions as the support tube fixing member.

As described in Embodiment 1, the camera side cable 12 is connected to the equipment side cable 16 via the cable connector 15. In the embodiment, in order to lock the camera side cable 12 to the camera support tube 13, as illustrated in FIGS. 10(g) and 10(h), the cable fastener 43 (locking member) is provided at the end part 13b on the outside of the body of the camera support tube 13.

According to the embodiment, by fixing the camera side cable 12 to a bottom part (a part having a narrowed width) of the longitudinal groove 43a of the cable fastener 43, it is possible to fix the camera side cable 12 to the camera support tube 13.

Therefore, according to the embodiment, after the camera side cable 12 and the camera support tube 13 are fixed by the cable fastener 43 as illustrated in FIG. 10(h), by fixing the camera side cable 12 by the adhesive tape 46 or the like as illustrated in FIG. 20(c), it is possible to fix the position of the camera support tube 13.

<Method for Installing Camera System for Monitoring Inside of Body 1>

Next, both the method for installing the imaging apparatus 2 in the camera system for monitoring the inside of a body 1 according to the embodiment, and the method of use, will be described. In addition, description of parts which are common to those in the installation method of Embodiment 1 will be omitted.

FIGS. 18(a) to 18(d) and FIGS. 19(a) to 19(d) are schematic views illustrating the method for installing the imaging apparatus 2 in the camera system for monitoring the inside of a body 1 according to the embodiment, in a process order. In addition, FIGS. 18(a) to 18(d) and FIGS. 19(a) to 19(d) illustrate a method for guiding one end part 13a of the camera support tube 13 toward the inside of the body by making the camera support tube 13 penetrate the inside of the cannula 31 using the cannula 31.

As illustrated in FIG. 18(a), first, the practitioner opens the ports 41a to 41d (holes) for inserting the forceps or the endoscope into the body cavity on the body wall 41, and inserts each of the plural trocars 32 (hereinafter, referred to as trocars 32a to 32c) into the ports 41a to 41c. Furthermore, the cannula 31 is inserted into the port 41d. In opening the hole of the port 41d, inserting the cannula 31 and opening the hole may be performed at the same time, for example, by using the cannula 31 which inserts the puncturing device 6.

In addition, here, for example, the insertion into the body wall may be performed only by using a device having a puncturing function, such as the trocar, instead of the cannula 31, and in the next process, the wire-like drawing auxiliary tool 7 may be directly inserted into the trocar.

Next, as illustrated in FIG. 18(b), the wire-like drawing auxiliary tool 7 is inserted, and the connection unit 8 is out of the tip end of the puncturing device 6.

As illustrated in FIG. 18(c), the practitioner inserts the endoscope 34 into the body cavity through the trocar 32c, and grips the connection unit 8 by the forceps 33 while observing the inside of the body using the endoscope 34, and as illustrated in FIG. 18(d), the connection unit 8 and the wire unit 9 are drawn out toward the outside of the body from the trocar 32b. Since the pulling unit 10 is present at one more end part, the wire is not mistakenly dropped, and the operation can be stably performed.

Next, as illustrated in FIG. 19(a), the camera side cable 12 is connected as illustrated in FIG. 5(c).

Next, as illustrated in FIG. 19(b), while pulling the pulling unit 10, the camera unit 11 is gripped by the forceps 33, and the trocar 32b is inserted into the body cavity through the trocar 32b.

Next, as illustrated in FIG. 19(c), while further pulling the pulling unit 10, and extracting the puncturing device 6 from the body wall 41, the camera unit 11 is pulled up to the installation position of the body wall, and is fixed by using a cable fastener 43.

Next, while further pulling the pulling unit 10, and extracting the puncturing device 6 from the body wall 41, as illustrated in FIG. 17(d), the camera side cable 12 which is guided toward the outside of the body passes through the inside of the camera support tube 13 from the slit 223 of the camera support tube 13. At this time, as illustrated in FIG. 17(e), a part of the cable connector 15 may be exposed from the slit 223 of the camera support tube 13.

Furthermore, as illustrated in FIG. 17(f), the camera support tube 13 is inserted into the cannula 31, and as illustrated in FIG. 19(c), the camera support tube 13 and the support tube joining unit 14 are joined to each other by a method of screwing or inserting. In addition, in a case where the camera side cable 12 and the cable connector 15 can pass through the inside of the puncturing device 6, the puncturing device 6 may be used as the camera support tube 13.

In a case of screwing, as illustrated in FIG. 19(d), after fixing the camera side cable 12 and the camera support tube 13 by the cable fastener 43, the camera unit 11 is pulled up to the installation position of the body wall by using the camera support tube 13, and the camera support tube 13 is fixed to the cannula 31 by using the stopper 77.

Next, as illustrated in FIG. 19(d), the drawing auxiliary tool 7 is removed, the camera side cable 12 and the extending cable 16a are connected to each other by the cable connector 15, and the extending cable 16a and the equipment side cable 16 are connected to each other by the cable connector 15a. Furthermore, since the extending cable or the equipment side cable do not pass through the inside of the body, the cable having a large diameter can be used.

Furthermore, in the installation method illustrated in FIGS. 18(a) to 18(d) and FIGS. 19(a) to 19(d), a method for guiding in the wire-like drawing auxiliary tool 7 through the puncturing device 6 is described, but the invention is not limited thereto, and after performing the puncturing in the process of FIG. 18(a), the puncturing device 6 is exchanged with the camera support tube 13, and the wire-like drawing auxiliary tool 7 may be guided in through the camera support tube 13. In addition, after performing the puncturing in the process of FIG. 18(a), the wire-like drawing auxiliary tool 7 is guided after the puncturing device 6 is extracted and only the cannula 31 remains, and the support tube 13 may be installed in the process of FIG. 19(c). In addition, the drawing auxiliary tool 7 may be guided in toward the trocar 32, by using the trocar 32 instead of the cannula 31.

<Method for Collecting Camera Unit 11>

An order of collecting the camera unit 11 after the surgery is finished, will be described.

First, the cable connector 15, the cable fastener 43, and the camera support tube 13 are removed, and the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out the cut organ.

<Effect>

In the embodiment, in a case where the practitioner changes the position of the camera support tube 13 after operating the camera support tube 13, adjusting the position of the camera support tube 13, and fixing the camera side cable 12 using the adhesive tape 46, the practitioner also operates the camera support tube 13 and adjusts the position of the camera support tube 13 again by peeling the adhesive tape 46. After this, again, the camera side cable 12 may be fixed by the 46.

In addition, for example, under the camera side cable 12 (that is, between the camera side cable 12 and the body surface 45), or according to the situation, under the cannula 31 or the camera support tube 13, by nipping an object having a desirable thickness similar to the support table 144 illustrated in FIG. 20(a), as a fixing height adjusting member, the fixing angle (inclination) of the cannula 31 connected to the camera side cable 12 and the camera support tube 13 may be changed. In other words, in the embodiment, the support tube fixing member may further be provided with the fixing height adjusting member which is not illustrated.

Accordingly, in a case where the camera side cable 12 is directly fixed by the adhesive tape 46, it is also possible for the camera support tube 13 to be fixed in a desirable state.

In addition, in the embodiment, a case where the cannula 31 illustrated in FIGS. 17(a) to 17(c) is used as the cannula 31 as described above, is illustrated as an example, but the camera support tube 13 according to the embodiment is not necessarily fixed to the cannula, and a general cannula can be used as the cannula.

In other words, in the embodiment, by fixing the camera side cable 12 to the camera support tube 13, and by fixing the camera side cable 12 to the outside of the body, it is possible to fix the camera support tube 13 using the camera side cable 12. In other words, by fixing the camera side cable 12 by the adhesive tape 46, the position and the orientation of the camera support tube 13 connected to the camera side cable 12 are fixed. Therefore, similar to a case where the camera support tube 13 is directly fixed to the outside of the body by the fixing tool, the camera support tube 13 may not be fixed to the cannula.

In addition, in the embodiment, as described above, a case where the camera support tube 13 is fixed by fixing the camera side cable 12 to the camera support tube 13 using the cable fastener 43, and by fixing the camera side cable 12 to the outside of the body by the adhesive tape 46, is described as an example. However, the embodiment is not limited thereto, and the camera support tube 13 or the cannula 31, and the camera side cable 12 may be fixed to the outside of the body by the fixing tool, such as the adhesive tape, after fixing the camera side cable 12 to the camera support tube 13 using the cable fastener 43 as described above. It is needless to say that two or more of the camera side cable 12, the camera support tube 13, and the cannula 31 may be fixed. In any case, by fixing the camera side cable 12 to the camera support tube 13 using the cable fastener 43, it is also possible to obtain an effect that improvement of workability and prevention of the camera side cable from being cut are possible, as described above.

In the embodiment, a case where the adhesive tape 46 is used in fixing the camera side cable 12 or the camera support tube 13, or the cannula 31, is described. However, the fixing tool is not limited thereto, and in other embodiments, it is also needless to say that a fixing tool similar to the fixing tool used in fixing the camera support tube 13 or the cannula 31 can be used.

In addition, even when a string-like member fixing unit (for example, a fixing unit which can fix the string-like member by making the string-like member pass or by binding the string-like member) which prevents the movement of the string-like member in the axial direction of the camera support tube 13 is provided in the camera support tube 13, similar effects can be obtained.

CONCLUSION

A camera system for monitoring the inside of a body (1) according to aspect 1 of the present invention includes: an imaging part (camera unit 11) for monitoring the inside of a body; a cable (camera side cable 12) which is connected to the imaging part, and is drawn out toward the outside of the body through the support tube; a control system (3) which is on the outside of the body, is connected to the cable, and includes at least a display apparatus (display 18); and a wire-like drawing auxiliary tool which guides the imaging part and the cable toward the inside of the body, and is used for pulling out the cable end part toward the outside of the body.

In the camera system for monitoring the inside of a body (1) according to aspect 2 of the present invention, in the above-described aspect 1, one end part 13*a* has the support tube (camera support tube 13) which is guided toward the inside of the body, and a joining unit (support tube joining unit 14) which is joined to the support tube, and the imaging part (camera unit 11) joined to the support tube on the inside of the body is provided. In addition, as the support tube, the puncturing device 6 may be used.

In the camera system for monitoring the inside of a body (1) according to aspect 3 of the present invention, in the above-described aspect 2, a bushing (cannula 31) having a tube-like structure which can insert the support tube therein may be provided, the support tube may be fixed to the bushing on the outside of the body, and the fixing member may fix the support tube by fixing the bushing to the body surface.

A method for installing the camera system for monitoring the inside of a body according to aspect 4 of the present invention, includes: a process of opening a hole on a body wall of an imaging part installation position of the camera system for monitoring the inside of a body by using a needle-like puncturing device, from the outside of the body; a process of pushing out a wire-like drawing auxiliary tool from a tip end of a pipe-like puncturing device inserted into the inside of the body; a process of clamping and drawing out a tip end part of the wire-like drawing auxiliary tool which is on the inside of the body, by using gripping forceps inserted from the outside of the body; a process of connecting the tip end part of the wire-like drawing auxiliary tool and an end part of a cable (camera side cable 12) connected to an imaging part (camera unit 11), on the outside of the body; a process of pulling one more side of the wire-like drawing auxiliary tool which is out of body from an imaging part installation position, and drawing in the cable connected to the wire-like drawing auxiliary tool and the imaging part toward the inside of the body; a process of drawing out the entire wire-like drawing auxiliary tool toward the outside of the body, and drawing out the end part of the cable toward the outside of the body; a process of fixing the drawn-out cable on the outside of the body; and a process of removing the connection of the wire-like drawing auxiliary tool, and electrically connecting the cable to a control system (3) which is on the outside of the body and includes at least a display apparatus (display 18).

The method for installing the camera system for monitoring the inside of a body according to aspect 5 of the present invention, in the above-described aspect 4, further includes: a process of making one end part 13*a* pass through the support tube (camera support tube 13) guided toward the inside of the body after drawing out the cable guided toward the inside of the body toward the outside of the body; a process of joining the imaging part and the support tube to each other by a joining unit (support tube joining unit 14) provided in the imaging part, on the inside of the body; and a process of adjusting the length of the support tube, the rotational direction of the support tube, and the inclination of the support tube with respect to the body surface, on the inside of the body, and directly or indirectly fixing the support tube to the body surface.

The method for installing the camera system for monitoring the inside of a body according to aspect 6 of the present invention, in the above-described aspect 4, further includes: a process of joining the imaging part and the puncturing device by the joining unit (support tube joining unit 14) provided in the imaging part, using the puncturing device 6 as the support tube (camera support tube 13) after drawing out the cable guided toward the inside of the body toward the outside of the body, on the inside of the body; and a process of adjusting the length of the support tube, the rotational direction of the support tube, and the inclination of the support tube with respect to the body surface, on the inside of the body, and directly or indirectly fixing the support tube to the body surface.

The method for installing the camera system for monitoring the inside of a body according to aspect 7 of the present invention, in the above-described aspect 5 or 6, includes: a process of guiding the bushing (cannula 31) having a tube-like structure which can insert the support tube and the puncturing device therein, together with the puncturing device 6, when opening the body wall.

Modification Example

The method for installing the camera system for monitoring the inside of a body of the present invention is not limited to a case of installing a camera system on the inside of the body of a human being, and can also be employed in a case of installing a camera system on the inside of an animal other than a human being.

In addition, the camera system for monitoring the inside of a body may be provided with connection determining means (not illustrated) which detects that the cable connector 15 is connected to the connection unit 8, and a pulling means (not illustrated) which pulls the pulling unit 10. The camera system for monitoring the inside of a body may be operated as follows.

First, in a state where the wire-like drawing auxiliary tool 7 is disposed to pass via the puncturing device 6, the inside of the body, and the trocar 32*b*, the connection determining means detects that the cable connector 15 is connected to the connection unit 8.

The connection determining means, for example, may be provided in the connection unit 8, and may detect the connection from a similar aspect if it is possible to detect that the cable connector 15 is connected (fixed) to the connection unit 8. In addition, when the connection determining means detects that the cable connector 15 is connected (fixed) to the connection unit 8, a detection signal may be sent.

Secondly, after the connection determining means detects that the cable connector 15 is connected to the connection unit 8, the pulling means guides the camera unit 11 toward the inside of the body by pulling the pulling unit 10. The pulling means, for example, can rotate around the rotation axis, and may have a structure in which the wire-like drawing auxiliary tool 7 is wound around in the periphery thereof. The pulling means may be operated by receiving the detection signal from the connection determining means.

In order to solve the above-described problems, there is provided a camera system for monitoring the inside of a body according to an aspect of the present invention, including: an imaging part for monitoring the inside of a body; a control system which is provided on the outside of the body, and includes at least a display apparatus; a cable which is capable of communicating between the imaging part and the control system; and an auxiliary device having a wire structure, in which the auxiliary device guides the imaging part and the cable in which one end part is connected to the imaging part from the outside of the body toward the inside of the body via a first hole provided on a body wall, and draws the other end part of the cable from the inside of the body toward the outside of the body via a second hole provided on the body wall.

There is provided an auxiliary device according to another aspect of the present invention which is used for installing an imaging part on the inside of the body, in a camera system for monitoring the inside of a body including the imaging part for monitoring the inside of a body, a control system which is provided on the outside of the body, and includes at least a display apparatus, and a cable which is capable of communicating between the imaging part and the control system, the auxiliary tool including: a wire structure, in which the imaging part and the cable in which one end part is connected to the imaging part are guided from the outside of the body toward the inside of the body via a first hole provided on a body wall, and the other end part of the cable is drawn out from the inside of the body toward the outside of the body via a second hole provided on the body wall.

In order to solve the above-described problems, there is provided a method for installing a camera system for monitoring the inside of a body according to still another aspect of the present invention, which is a method for installing a camera system for monitoring the inside of a body including an imaging part for monitoring the inside of a body, a control system which includes at least a display apparatus, and a cable which is capable of communicating between the imaging part and the control system, the method including: a process of providing a first hole on a body wall by using a puncturing device having a cavity on the inside thereof; a process of inserting one end part of a wire-like auxiliary device into the inside of the body via the first hole; a process of drawing out the one end part of the auxiliary device toward the outside of the body via a second hole provided on the body wall; a process of connecting the one end part of the auxiliary device and the cable connected to the imaging part on the outside of the body; a process of drawing in the imaging part and the cable into the inside of the body via the second hole by pulling the other end part of the auxiliary device, and drawing out the end part of the cable toward the outside of the body via the first hole; and a process of releasing the connection of the one end part of the auxiliary device and the cable, and electrically connecting the end part of the cable to the control system.

Advantageous Effects of Invention

Summary of Embodiments

A camera system for monitoring the inside of a body (1), according to aspect 1A of the present invention includes: an imaging part (camera unit 11) for monitoring the inside of a body; a control system (3) which is provided on the outside of the body, and includes at least a display apparatus (display 18); a cable (camera side cable 12) which is capable of communicating between the imaging part and the control system; and an auxiliary device (wire-like drawing auxiliary tool 7) having a wire structure, in which the auxiliary device guides the imaging part and the cable in which one end part is connected to the imaging part from the outside of the body toward the inside of the body via a first hole provided on a body wall, and draws out the other end part of the cable from the inside of the body toward the outside of the body via a second hole provided on the body wall.

In the camera system for monitoring the inside of a body according to aspect 2A of the present invention, in the above-described aspect 1, the auxiliary device may be provided with a wire unit (wire unit 9) and a connection unit (8) provided at one end part of the wire unit, a connector (cable connector 15) may be provided at the other end part of the cable, and the connection unit may have a shape which is capable of fixing the connector. In addition, the camera system for monitoring the inside of a body is also referred to as a camera system for monitoring the inside of a body in which the imaging part is guided toward the inside of the body, as one end of the wire unit is drawn out toward the outside of the body via a first body wall hole, the inside of the body, and a second body wall hole from the outside of the body, in a state where the auxiliary device for guiding the imaging part toward the inside of the body includes the wire unit, and the cable is connected to one end of the wire unit.

In the camera system for monitoring the inside of a body according to aspect 3A of the present invention, in the above-described aspect 2, the outer diameters of the wire unit and the connection unit may be equal to or less than the outer diameter of the connector.

In the camera system for monitoring the inside of a body according to aspect 4A of the present invention, in the above-described aspect 2 or 3, a puncturing device (6) for providing the second hole on the body wall may further be provided, the puncturing device has a shape of a pipe, and the inner diameter of the puncturing device may be greater than the outer diameters of the wire unit, the connection unit, and the cable.

In the camera system for monitoring the inside of a body according to aspect 5A of the present invention, in the above-described aspect 2 or 3, a puncturing device (6) for providing the second hole on the body wall may further be provided, and the outer diameter of the puncturing device may be equivalent to the outer diameter of the cable.

In the camera system for monitoring the inside of a body according to aspect 6A of the present invention, in any of the above-described aspects 2 to 5, the auxiliary device may be provided with a pulling unit provided at the other end part of the wire unit, and the outer diameter of the pulling unit may be greater than the inner diameter of the second hole.

In the camera system for monitoring the inside of a body according to aspect 7A of the present invention, in any of the above-described aspects 2 to 6, a connection unit protection cap (protection cap 20) which protects the connection unit may further be provided, and the connection unit protection cap may include a part which corresponds to a shape of the connector.

In the camera system for monitoring the inside of a body according to aspect 8A of the present invention, in the above-described aspect 4 or 5, the puncturing device may function as a support tube which supports the imaging part as being fixed to the imaging part.

An auxiliary device (wire-like drawing auxiliary tool 7) according to aspect 9A of the present invention which is used for installing the imaging part on the inside of the body, in a camera system for monitoring the inside of a body (1) including the imaging part (camera unit 11) for monitoring the inside of a body, a control system (3) which is provided on the outside of the body, and includes at least a display apparatus (display 18), and a cable (camera side cable 12) which is capable of communicating between the imaging part and the control system, the auxiliary device, includes: a wire structure, and the imaging part and the cable in which one end part is connected to the imaging part are guided from the outside of the body toward the inside of the body via a first hole provided on a body wall, and the other end part of the cable is drawn out from the inside of the body toward the outside of the body via a second hole provided on the body wall.

A method for installing a camera system for monitoring the inside of a body according to aspect 10A of the present invention which is a method for installing a camera system for monitoring the inside of a body (1) including an imaging part (camera unit 11) for monitoring the inside of a body, a control system (3) which includes at least a display apparatus (display 18), and a cable (camera side cable 12) which is capable of communicating between the imaging part and the control system, the method includes: a process of providing a first hole on a body wall by using a puncturing device (6) having a cavity on the inside thereof; a process of inserting one end part of a wire-like auxiliary device (wire-like drawing auxiliary tool 7) into the inside of the body via the first hole; a process of drawing out the one end part of the auxiliary device toward the outside of the body via a second hole provided on the body wall; a process of connecting the one end part of the auxiliary device and the cable connected to the imaging part on the outside of the body; a process of drawing in the imaging part and the cable toward the inside of the body via the second hole by pulling the other end part of the auxiliary device, and drawing out the end part of the cable toward the outside of the body via the first hole; and a process of releasing the connection of the one end part of the auxiliary device and the cable, and electrically connecting the end part of the cable to the control system.

A method for operating a camera system for monitoring the inside of a body according to aspect 10B of the present invention which is a method for operating a camera system for monitoring the inside of a body (1) including an imaging part (camera unit 11) for monitoring the inside of a body, a control system (3) which includes at least a display apparatus (display 18), and a cable (camera side cable 12) which is capable of communicating between the imaging part and the control system, in which the camera system for monitoring the inside of a body includes the auxiliary device (wire-like drawing auxiliary tool 7) for guiding the imaging part toward the inside of the body, the auxiliary device includes a wire unit, a connection unit which can connect a connector of the cable to one end part of the wire unit is provided, in which the camera system for monitoring the inside of a body further includes connection determining means which detects that the connector is connected to the connection unit, and pulling means which pulls the other end part of the wire unit, and in which, in a state where the wire unit is disposed via the first hole provided on the body wall, the inside of the body, and the second wall provided on the body wall, after a process of detecting that the connector is connected to the connection unit by the connection determining means, and the connection determining means detects that the connector is connected to the connection unit, the pulling means guides the imaging part toward the inside of the body by pulling the other end part of the wire unit.

In the method for installing a camera system for monitoring the inside of a body according to aspect 11A of the present invention, in the above-described aspect 10, the first hole may be provided on the body wall in a state where the auxiliary device is disposed in a cavity on the inside of the puncturing device.

The method for installing a camera system for monitoring the inside of a body according to aspect 12A of the present invention, in the above-described aspect 10 or 11, may include: a process of connecting the imaging part and the support tube (camera support tube 13) for fixing the imaging part to each other on the inside of the body; a process of adjusting at least one selected from a group made of the length of the support tube, the rotational direction of the support tube, and the inclination of the support tube with respect to the body surface, on the inside of the body; and a process of directly or indirectly fixing the support tube to the body surface.

In the method for installing a camera system for monitoring the inside of a body according to aspect 13A of the present invention, in the above-described aspect 12, the puncturing device may be used as the support tube.

The present invention is not limited to each of the above-described embodiments, various changes are possible within the range described in claims, and an embodiment which can be obtained by appropriately combining technical means which are respectively disclosed in different embodiments is also included in the technical range of the present invention. Furthermore, by combining the technical means which are respectively disclosed in each embodiment, it is possible to form new technical characteristics.

INDUSTRIAL APPLICABILITY

The imaging apparatus can be appropriately employed in endoscopic surgery or the like.

REFERENCE SIGNS LIST

1 CAMERA SYSTEM FOR MONITORING INSIDE OF BODY
2 IMAGING DEVICE
3 CONTROL SYSTEM
4 CONNECTION UNIT
5 DRAWING AUXILIARY TOOL
6 PUNCTURING DEVICE
7 DRAWING AUXILIARY TOOL
8 CONNECTION UNIT
9 WIRE UNIT
10 PULLING UNIT
11 CAMERA UNIT
12 CAMERA SIDE CABLE
13 CAMERA SUPPORT TUBE
13a, 13b END PART
14 SUPPORT TUBE JOINING UNIT
15 CABLE CONNECTOR
15a CABLE CONNECTOR
16 EQUIPMENT SIDE CABLE
16a EXTENDING CABLE
17 CAMERA UNIT CONTROL EQUIPMENT
18 DISPLAY
19 CIRCUIT BOARD
20 PROTECTION CAP
21 CAMERA HOUSING
22 SUPPORT UNIT
23 LOCKING FEMALE SCREW
24 IMAGING UNIT
25 SOLID-STATE IMAGING ELEMENT
26 LENS
27 ILLUMINATION APPARATUS
28 CONTROL CIRCUIT
31 CANNULA
31a, 31b END PART
32, 32a to 32c TROCAR
33, 33a to 33c FORCEPS
34 ENDOSCOPE
36 OBTURATOR (SHARPENED ROD)
37 VALVE
41 BODY WALL
41a to 41c PORT

43 CABLE FASTENER (FIXING MEMBER)
43a LONGITUDINAL GROOVE
45 BODY SURFACE
46 ADHESIVE TAPE (FIXING MEMBER)
77 STOPPER
113 HEAD UNIT
114 LEG UNIT
123 LOCKING MALE SCREW
131 HEAD UNIT
132 LEG UNIT
141 FIXING DEVICE (FIXING MEMBER)
144 SUPPORT TABLE
145 BAND
145a FIXING END
146 ADJUSTER
223 SLIT
323 LOCKING HOLE
423 LOCKING CLAW
523 LOCKING CLAW
623 LOCKING HOLE

The invention claimed is:

1. A camera system for monitoring an inside of a body, comprising:
  a camera;
  a cable including a first end portion and a second end portion located opposite to the first end portion, the first end portion being connected to the camera and the second end portion including a first connector;
  a drawing auxiliary tool including: (i) a wire including a third end portion and a fourth end portion located opposite to the third end portion, and (ii) a second connector provided at the third end portion; and
  a second connector protection cap that protects the second connector, wherein
  the fourth end portion remains outside of the body;
  the third end portion is structured to be:
    inserted within the body through a first hole in the body,
    drawn out of the body through a second hole in the body so that the first connector is fixable to the second connector outside of the body,
    pulled from the fourth end portion so that the camera and the second end portion are guidable from the outside of the body toward the inside of the body through the second hole, and
    further pulled from the fourth end portion so that the second end portion is drawn out from the inside of the body toward the outside of the body through the first hole;
  the camera is operable to monitor the inside of the body; and
  the second connector protection cap includes a portion which has a shape that matches a shape of the first connector.

2. The camera system for monitoring an inside of a body according to claim 1,
  wherein the second connector is structured to fix the first connector to the second connector.

3. The camera system for monitoring an inside of a body according to claim 1,
  wherein respective outer diameters of the wire and the second connector are equal to or smaller than an outer diameter of the first connector.

4. The camera system for monitoring an inside of a body according to claim 1, further comprising:
  a puncturing pipe that provides the first hole in the body,
  wherein the puncturing pipe has an inner diameter greater than respective outer diameters of the wire, the second connector, and the cable.

5. The camera system for monitoring an inside of a body according to claim 1, further comprising:
  a puncturing pipe that provides the first hole in the body,
  wherein an outer diameter of the puncturing pipe is equivalent to an outer diameter of the cable.

6. The camera system for monitoring an inside of a body according to claim 1,
  wherein the drawing auxiliary tool is further provided with a puller provided at the fourth end portion of the wire, and
  wherein an outer diameter of the puller is greater than an inner diameter of the first hole.

* * * * *